US012773537B1

(12) United States Patent
White et al.

(10) Patent No.: US 12,773,537 B1

(45) Date of Patent: Oct. 27, 2026

(54) SYSTEMS AND METHODS FOR A SHUNT CATHETER CLIP

(71) Applicant: Dignity Health, San Francisco, CA (US)

(72) Inventors: Michael White, San Francisco, CA (US); Dakota Graham, San Francisco, CA (US)

(73) Assignee: Dignity Health, San Francisco (CA)

( * ) Notice: Subject to any disclaimer, the term of this patent is extended or adjusted under 35 U.S.C. 154(b) by 623 days.

(21) Appl. No.: 17/816,679

(22) Filed: Aug. 1, 2022

Related U.S. Application Data

(60) Provisional application No. 63/227,361, filed on Jul. 30, 2021.

(51) Int. Cl.

| | |
|---|---|
| ***F16B 2/20*** | (2006.01) |
| ***A61M 27/00*** | (2006.01) |
| ***A61M 39/28*** | (2006.01) |
| ***F16B 2/10*** | (2006.01) |
| ***F16B 2/24*** | (2006.01) |
| ***F16L 33/02*** | (2006.01) |
| ***F16L 33/025*** | (2006.01) |
| ***F16L 33/03*** | (2006.01) |
| ***F16L 33/035*** | (2006.01) |

(52) U.S. Cl.
CPC ........ *A61M 27/002* (2013.01); *A61M 39/284* (2013.01); *F16B 2/10* (2013.01); *F16B 2/248* (2013.01); *F16L 33/02* (2013.01); *F16L 33/025* (2013.01); *F16L 33/03* (2013.01); *F16L 33/035* (2013.01)

(58) Field of Classification Search
CPC .. A61M 27/002; A61M 39/28; A61M 27/006; A61M 2025/024; F16B 2/10; F16B 2/248; F16B 45/06; F16B 2/20; F16L 33/02; F16L 33/025; F16L 33/03; F16L 33/035; A61B 17/1227; A61B 2017/2808; A61B 17/2812; A61B 17/083; A61B 17/122
See application file for complete search history.

(56) References Cited

U.S. PATENT DOCUMENTS 770,982 A * 9/1904 Plassmann ............. F16L 27/111 285/241
3,166,819 A * 1/1965 Robbins ................ A61M 25/02 285/244
4,192,315 A * 3/1980 Hilzinger ........... A61B 17/1227 24/565

(Continued)

*Primary Examiner* — Courtney Fredrickson
*Assistant Examiner* — Anna E Vargas
(74) *Attorney, Agent, or Firm* — Polsinelli PC

(57) ABSTRACT

A catheter clip can circumferentially close around a catheter and secure the catheter to a shunt valve of a shunt valve system. The catheter clip provides easier application without the need to manipulate the shunt system and risk displacement or movement of the proximal catheter. The catheter clip applies a consistent circumferential force around the catheter to ensure that the catheter is appropriately secured and eliminate the risk of human-error that comes with tying a tight and secure knot. Finally, the catheter clip is durable and lasts for the lifetime of the shunt, ensuring that the catheter is securely connected to the shunt valve and reducing risk for disconnection and shunt malfunction.

18 Claims, 31 Drawing Sheets

(56) References Cited

U.S. PATENT DOCUMENTS

| | | | | | |
|---|---|---|---|---|---|
| 4,827,930 | A * | 5/1989 | Kees, Jr. | A61B 17/1227 | 606/142 |
| 6,293,796 | B1 * | 9/2001 | Trom | A61C 5/85 | 433/155 |
| 2021/0322041 | A1 * | 10/2021 | Looi | A61M 27/002 | |

* cited by examiner

10

100

200

200

300

400

400

SYSTEMS AND METHODS FOR A SHUNT CATHETER CLIP

CROSS-REFERENCE TO RELATED APPLICATIONS

This is a U.S. Non-Provisional Patent Application that claims benefit to U.S. Provisional Patent Application Ser. No. 63/227,361 filed 30 Jul. 2021, which is herein incorporated by reference in its entirety.

FIELD

The present disclosure generally relates to implantable medical tubes and in particular, to devices, systems and associated methods for a catheter clip that secures a catheter to a shunt valve.

BACKGROUND

Shunt catheters are often surgically implanted within the body to facilitate drainage and/or diversion of fluids from one area of the body to another. Common problems that arise with catheters is the tendency of catheters to become decoupled and/or dislodged from shunt systems during or after placement, requiring replacement by practitioners and potentially exposing a patient to additional risks. Typically, surgical placement of a catheter requires additional personnel to hold a shunt valve of the shunt system and other components in place while the practitioner secures the catheter to the shunt valve using a suture (e.g., thread) that is tied manually around the catheter where the catheter meets the shunt valve, which can be difficult especially in maneuvering the suture around the shunt valve while the shunt system is in its final position. Shunt valve systems are often meant to remain within the body for many years.

Disconnection of the catheter from a shunt valve following placement is a potentially life-threatening complication, requiring emergency shunt revision or placement of an external ventricular drain. Revision procedures can be traumatic to tissues and can add further monetary costs. Three primary causes of revision procedures for shunt system placement are as follows: (a) the suture that holds the catheter in place can break down over time; (b) the suture can be tied too loosely or too tight, causing disconnection of the catheter from the shunt system through movement, gravity, and/or severance of the catheter; and (3) non-ideal placement of the suture.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1A:
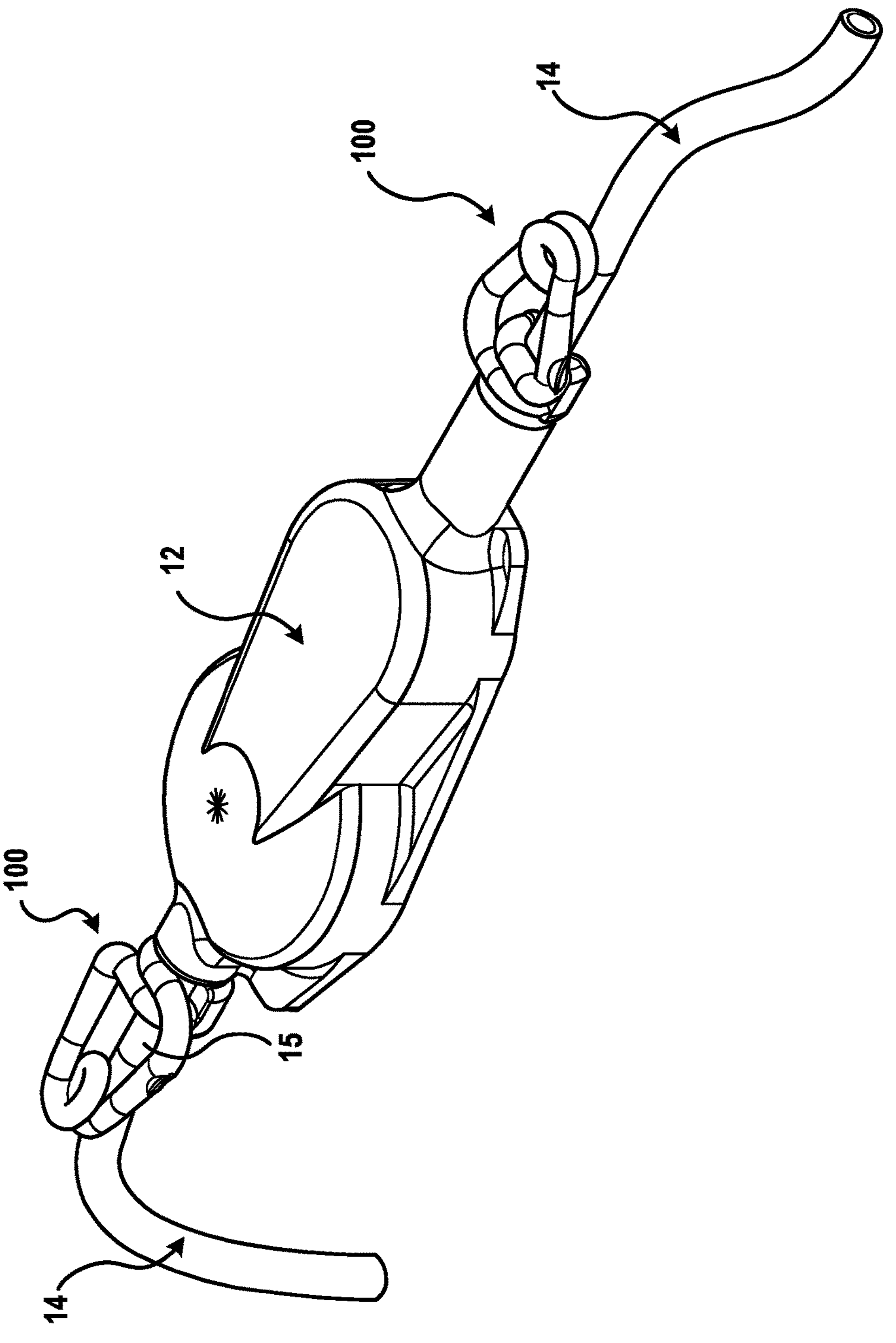
FIG. 1A is an illustration showing a perspective view of a shunt valve system including a catheter clip.
Figure 1B:
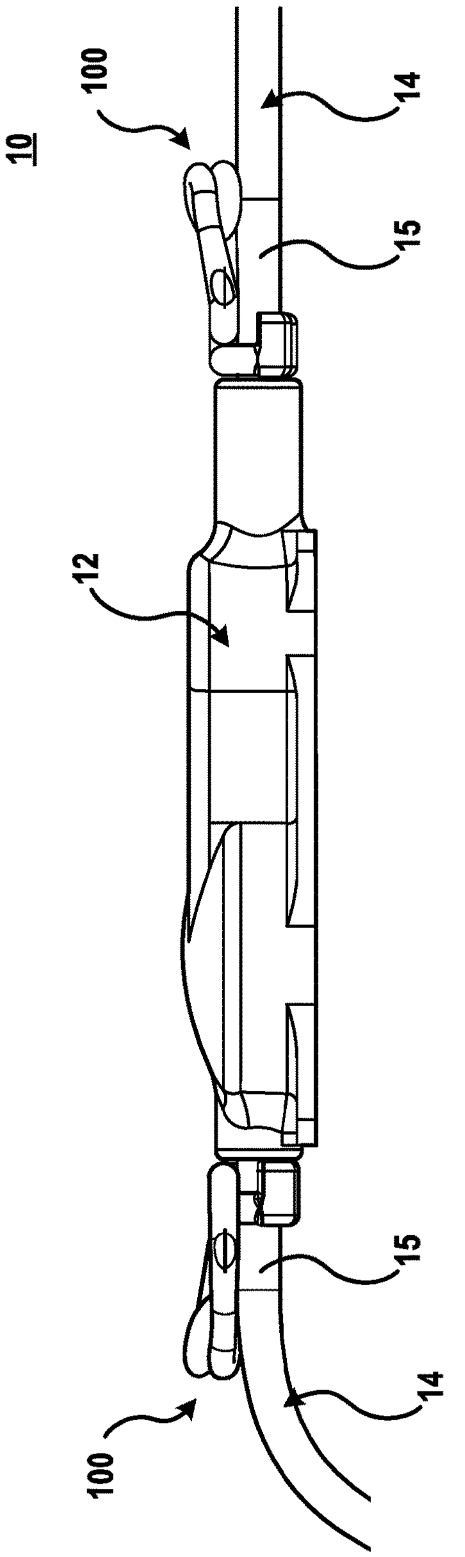
FIGS. 1B and 1C are a pair of illustrations showing side views of the shunt valve system and catheter clip of FIG. 1A.
Figure 1C:
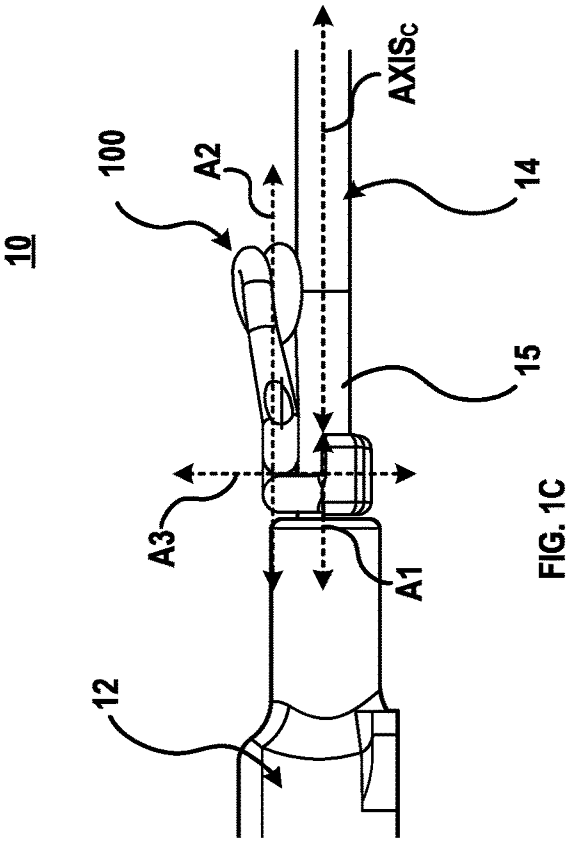
Figure 1D:
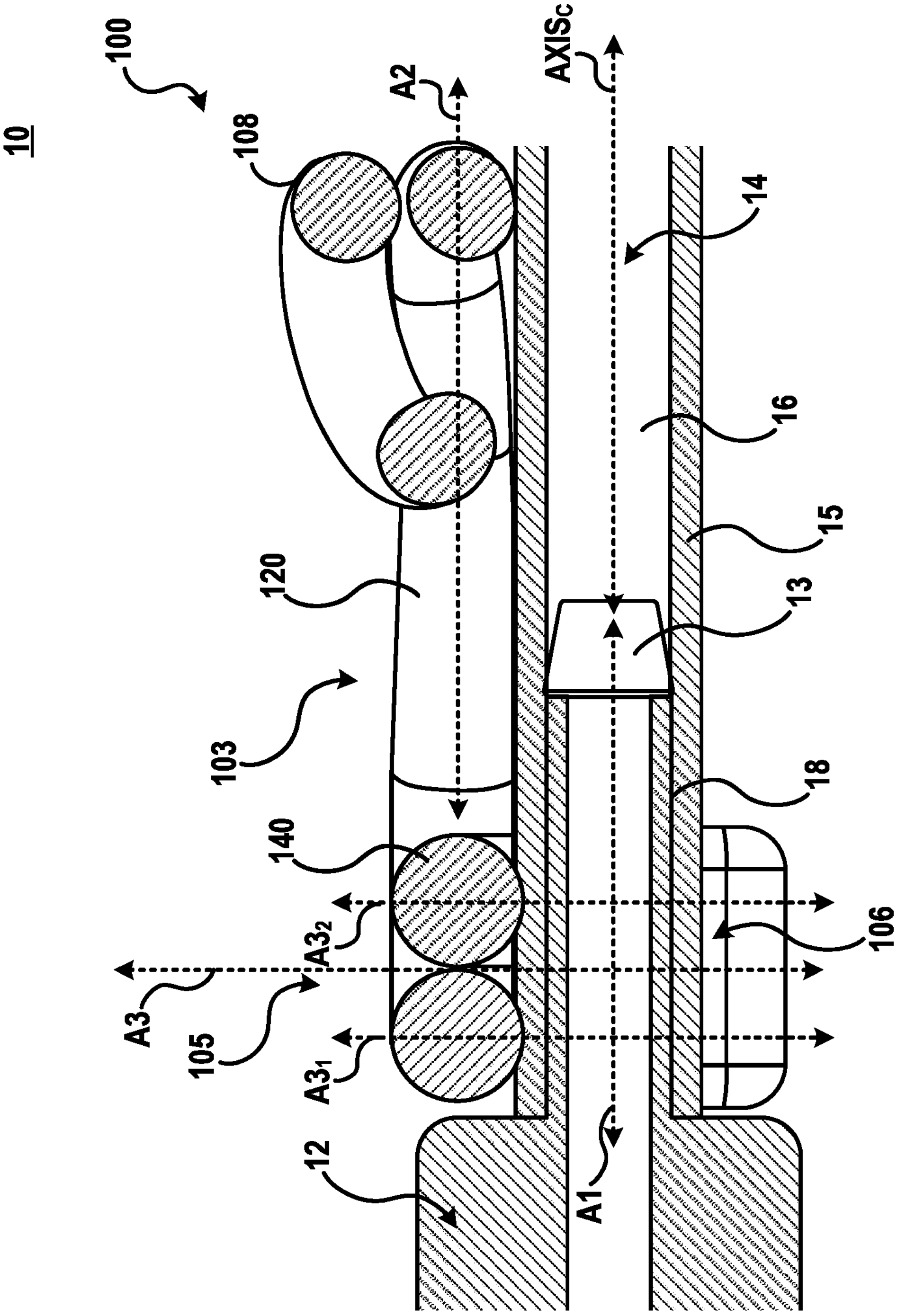
FIG. 1D is an illustration showing a cross-sectional side view of the shunt valve system and catheter clip of FIG. 1A.
Figure 1F:
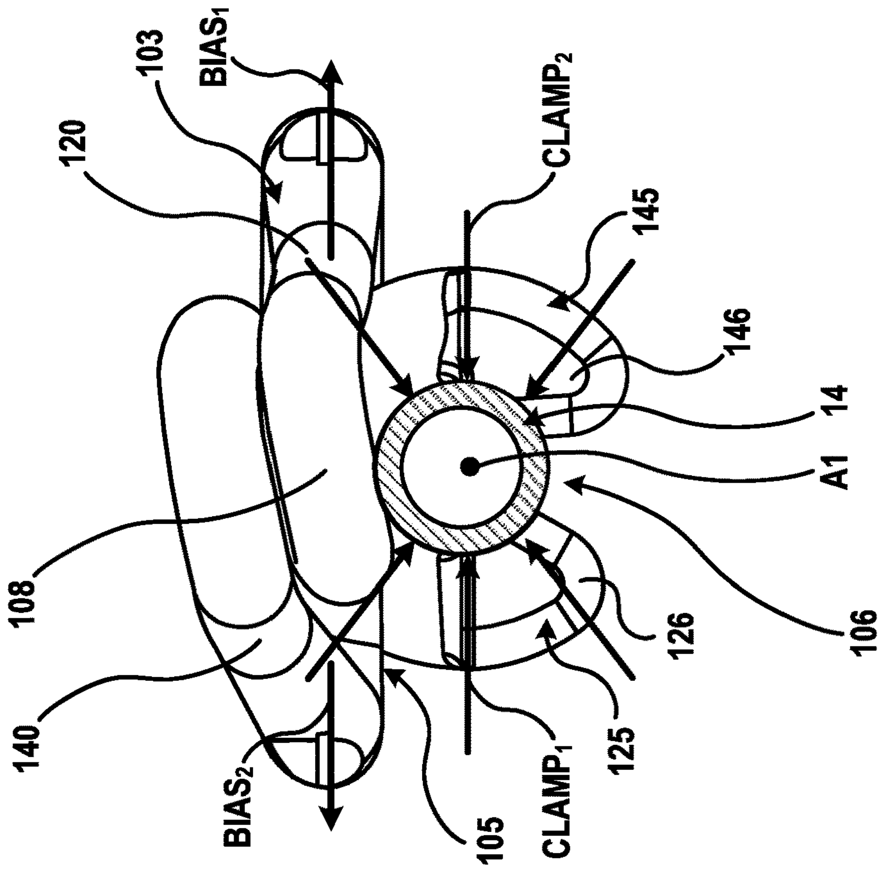
FIGS. 1E and 1F are a pair of illustrations showing respective front and rear views of the catheter clip of FIG. 1A coupled around a catheter of the shunt valve system.
Figure 1E:
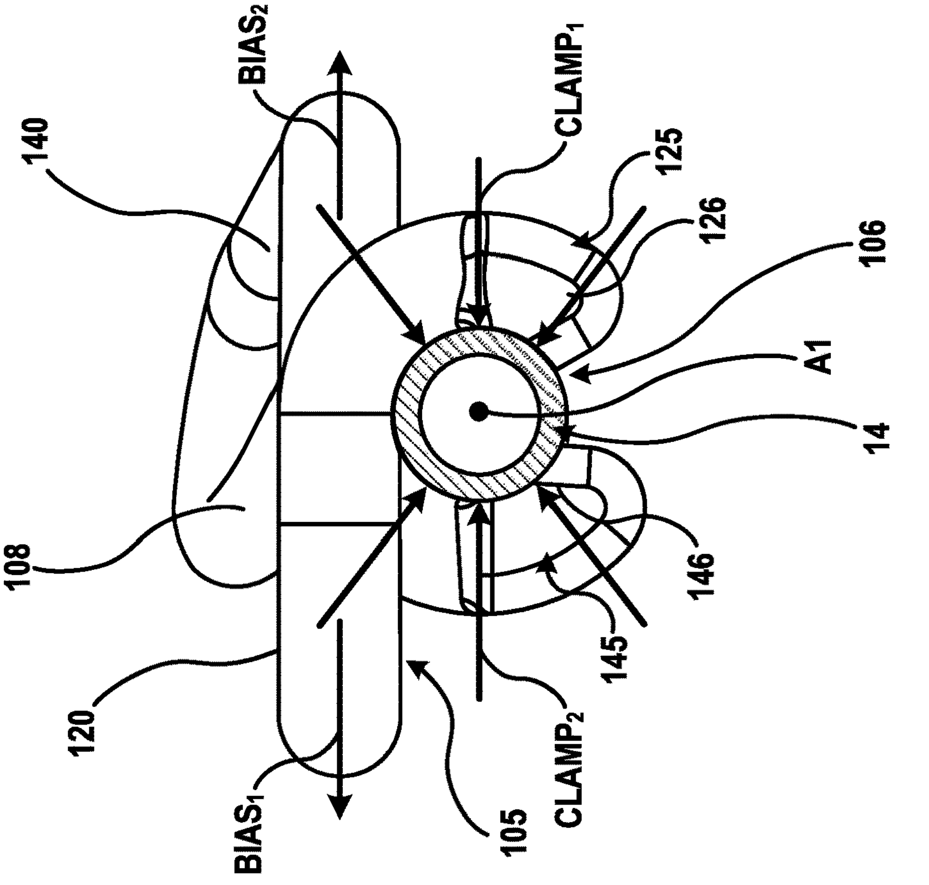

Various embodiments of a catheter clip for a shunt valve system are described herein. The catheter clip resolves common problems related to present "suturing" methods of securing a catheter to a shunt valve of the shunt valve system such as dislodgement or severance of the catheter within the body. The catheter clip is operable to circumferentially close around the catheter and secure the catheter to the shunt valve and is relatively quick and simple to apply during a procedure without the need to manipulate the shunt system and risk displacement or movement of the proximal catheter. The catheter clip is compatible with existing shunt valve systems. The catheter clip applies a consistent circumferential force to ensure that the catheter is appropriately secured and eliminates the risk of human-error that comes with tying a tight and secure knot. Further, the catheter clip enables easy removal during revision procedures (as opposed to cutting a suture). Finally, the catheter clip is durable and lasts for the lifetime of the shunt system, ensuring that the catheter is securely connected to the valve during the lifetime of the shunt system and reducing risk for disconnection and shunt malfunction.

With reference to FIGS. 1A-1F, a catheter clip 100 for a shunt valve system 10 enables secure connection between a catheter 14 and a shunt valve 12 of the shunt valve system 10. The catheter clip 100 includes a clip body 101 (FIGS. 2A-2F) that maintains a "low" profile against the catheter to reduce intrusiveness of the catheter clip within the body; the clip body 101 includes an elongated clamping portion 104 that captures the catheter 14 within an elongated clamping receptacle 106 and applies a clamping force (collectively, $CLAMP_1$ and $CLAMP_2$ in FIGS. 1E and 1F), the clamping force being a consistent circumferential force applied around the catheter 14 to ensure that the catheter 14 is appropriately secured without the need for silk ties or sutures. The elongated clamping receptacle 106 defines a circular cross-section configured to capture the catheter 14 and further defines a receptacle axis A1 that corresponds with a catheter axis $AXIS_C$ of the catheter 14 (e.g., a direction of elongation of the catheter 14) when the catheter 14 is captured at the elongated clamping receptacle 106. The clip body 101 includes a tensioning portion 108 that generates the clamping force such that the catheter clip 100 maintains a snug grip on the catheter 14 while decreasing the likelihood of disconnection or severance of the catheter 14. The catheter clip 100 can be compatible with existing shunt valve systems (such as shunt valve system 10) and can be used to secure catheters to shunt valves in lieu of sutures.

In a primary embodiment, the clip body 101 includes a pair of arms 102 including a first arm 120 and a second arm 140; the first arm 120 and the second arm 140 can be connected at the tensioning portion 108 and each terminate at the elongated clamping portion 104. In particular, the clip body 101 can be a single member that is "coiled" at the tensioning portion 108 to form the first arm 120 and the second arm 140 extending from the tensioning portion 108. In the embodiment shown, the tensioning portion 108 can form a torsion spring arrangement. As shown, the first arm 120 and the second arm 140 collectively define an elongated section 103 extending from the tensioning portion 108, the elongated section 103 defining a central body line A2 that is parallel with the receptacle axis A1. Due to this arrangement, the catheter clip 100 can firmly grasp the catheter 14 while maintaining a low profile that is in line with the shunt valve 12 and catheter 14. The first arm 120 can include a first terminal portion 125 having a first clamping element 126 defined opposite to the tensioning portion 108 and the second arm 140 can include a second terminal portion 145 having a second clamping element 146 and defined opposite to the tensioning portion 108; the first clamping element 126 and the second clamping element 146 can collectively define the elongated clamping receptacle 106 that captures the catheter 14 therein.

The tensioning portion 108 generates a biasing force (collectively, $BIAS_1$ and $BIAS_2$ in FIGS. 1E and 1F) that initially forces the first arm 120 and the second arm 140 apart; the first arm 120 and the second arm 140 can collectively define a crossed portion 105 that inverts the biasing force generated by the tensioning portion 108 into the clamping force that draws the first arm 120 and the second arm 140 together at the elongated clamping portion 104 to apply the clamping force around the catheter 14 when the catheter 14 is captured at the elongated clamping portion 104. A practitioner can transition the elongated clamping portion 104 from a first "closed" configuration (FIGS. 4A and 4C) to a second "open" configuration (FIGS. 4B and 4D) by pinching the pair of arms 102 together along the elongated section 103 and can transition the elongated clamping portion 104 from the second "open" configuration to the first "closed" configuration by releasing the pair of arms 102. The first arm 120 can include a first gripping portion 131 and the second arm 140 can include a second gripping portion 151 along the elongated section 103 that enable a practitioner to grasp the catheter clip 100 with an applicator or standard forceps.

In one method of securing the catheter 14 to the shunt valve 12, a practitioner can first connect an end portion 15 of the catheter 14 to the shunt valve 12. The shunt valve 12 includes a nipple portion 13 that extends from the shunt valve 12 for receipt of the catheter 14, and the catheter 14 includes a lumen 16 that captures the nipple portion 13 of the shunt valve 12 in a friction-fit engagement. As such, the catheter 14 can define an overlap region 18 where the nipple portion 13 of the shunt valve 12 is captured within the lumen 16. The practitioner can then grip the catheter clip 100 with an applicator or forceps and "pinch" the first arm 120 and the second arm 140 together to transition the elongated clamping portion 104 into the second open configuration. The practitioner can then position the catheter clip 100 around the catheter 14 such that the elongated clamping receptacle 106 is positioned around the catheter 14 along the overlap region 18 and the tensioning portion 108 is positioned away from the shunt valve 12, and can then release the first arm 120 and the second arm 140 to allow the elongated clamping receptacle 106 to apply the clamping force around the catheter 14 along the overlap portion 18. The catheter clip 100 can remain within the body during the life of the shunt valve system 10.

FIGS. 2A-2F illustrate a first embodiment of the catheter clip 100 without the shunt valve system 10 of FIGS. 1A-1F. As shown with additional reference to FIGS. 1A-1F, the catheter clip 100 includes the elongated clamping portion 104 having the elongated clamping receptacle 106 for capturing the catheter 14 therewithin; the elongated clamping receptacle 106 defines the receptacle axis A1 that aligns with the catheter axis $AXIS_C$ and applies the clamping force generated by the tensioning portion 108 when the catheter 14 is captured at the elongated clamping receptacle 106.

The catheter clip 100 includes the pair of arms 102 including the first arm 120 and the second arm 140 that transfer the forces generated at the tensioning portion 108; in particular the first arm 120 and the second arm 140 collectively define the elongated section 103 in which the first arm 120 and the second arm 140 extend away from the tensioning portion 108. The elongated section 103 defines the central body line A2 that is parallel with the receptacle axis A1 to provide a minimally-intrusive profile. In particular, the first arm 120 defines a first longitudinal portion 121 and the second arm 140 defines a second longitudinal portion 141 that collectively form the elongated section 103. As shown, the biasing force generated at the tensioning element initially force the first longitudinal portion 121 and the second longitudinal portion 141 away from one another as shown in FIG. 2F. In some embodiments, the first longitudinal portion 121 of the first arm 120 is slightly longer than the second longitudinal portion 141 of the second arm 140 to minimize a height profile of the catheter clip 100. Further, the first longitudinal portion 121 of the first arm 120 includes a first gripping portion 131 and the second longitudinal portion 141 of the second arm 140 includes a second gripping portion 151 for a practitioner to grip the catheter clip 100 for placement of the catheter clip 100 and to open the elongated clamping receptacle 106.

As shown, the first arm 120 and the second arm 140 also collectively define the crossed portion 105 in which the first arm 120 and the second arm 140 turn and extend in a lateral direction perpendicular to the central body line A2 and the receptacle axis A1. In particular, the first arm 120 includes a first lateral bend 122 and a first lateral portion 123, where the first lateral bend 122 serves as a transition between the first longitudinal portion 121 and the first lateral portion 123 of the first arm 120. Similarly, the second arm 140 includes a second lateral bend 142 and a second lateral portion 143, where the second lateral bend 142 serves as a transition between the second longitudinal portion 141 and the second lateral portion 143 of the second arm 140. Collectively, the first lateral portion 123 of the first arm 120 and the second lateral portion 143 of the second arm 140 define the crossed portion 105. Note that a direction of elongation of the first lateral portion 123 of the first arm 120 is opposite from a direction of elongation of the second lateral portion 143 of the second arm 140. With additional reference to FIG. 2F, the crossed portion 105 inverts respective directions of the biasing force generated at the tensioning portion 108 into the clamping force applied at the elongated clamping receptacle 106. As discussed, the first longitudinal portion 121 of the first arm 120 is slightly longer than the second longitudinal portion 141 of the second arm 140, as a result the first lateral portion 123 of the first arm 120 can be positioned farther away from the tensioning portion 108 than the second lateral portion 143 of the second arm 140 as shown.

The first arm 120 and the second arm 140 further collectively define the elongated clamping portion 104 opposite from the tensioning portion 108 that extends "downward" along a normal line A3 (FIGS. 2B-2D) towards the catheter 14 to capture the catheter 14 at the elongated clamping receptacle 106 of the elongated clamping portion 104. In particular, the first arm 120 includes a first terminal bend 124 and a first terminal portion 125, where the first terminal bend 124 serves as a transition between the first lateral portion 123 and the first terminal portion 125 of the first arm 120. As shown, the first terminal portion 125 defines a first normal line $A3_1$ associated with the normal line A3 that is perpendicular to the to the central body line A2 and the receptacle axis A1, and is also perpendicular to the direction of elongation of the first lateral portion 123. Similarly, the second arm 140 includes a second terminal bend 144 and a second terminal portion 145, where the second terminal bend 144 serves as a transition between the second lateral portion 143 and the second terminal portion 145 of the second arm 140. As shown, the second terminal portion 145 defines a second normal line $A3_2$ associated with the normal line A3 that is perpendicular to the to the central body line A2 and the receptacle axis A1, and is also perpendicular to the direction of elongation of the second lateral portion 143. As such, as illustrated with additional reference to FIGS. 1B-1D, the first terminal bend 124 and the second terminal bend 144 enable the clip body 101 to lie flat against the catheter 14 in the context of the shunt valve system 10. Because the first lateral portion 123 of the first arm 120 can be positioned farther away from the tensioning portion 108 than the second lateral portion 143 of the second arm 140 as shown in FIGS. 2C and 2D, the first normal line $A3_1$ is similarly positioned farther away from the tensioning portion 108 than the second normal line $A3_2$; the normal line A3 in this context can be defined as an average of the first normal line $A3_1$ and the second normal line $A3_2$.

Figure 2A:
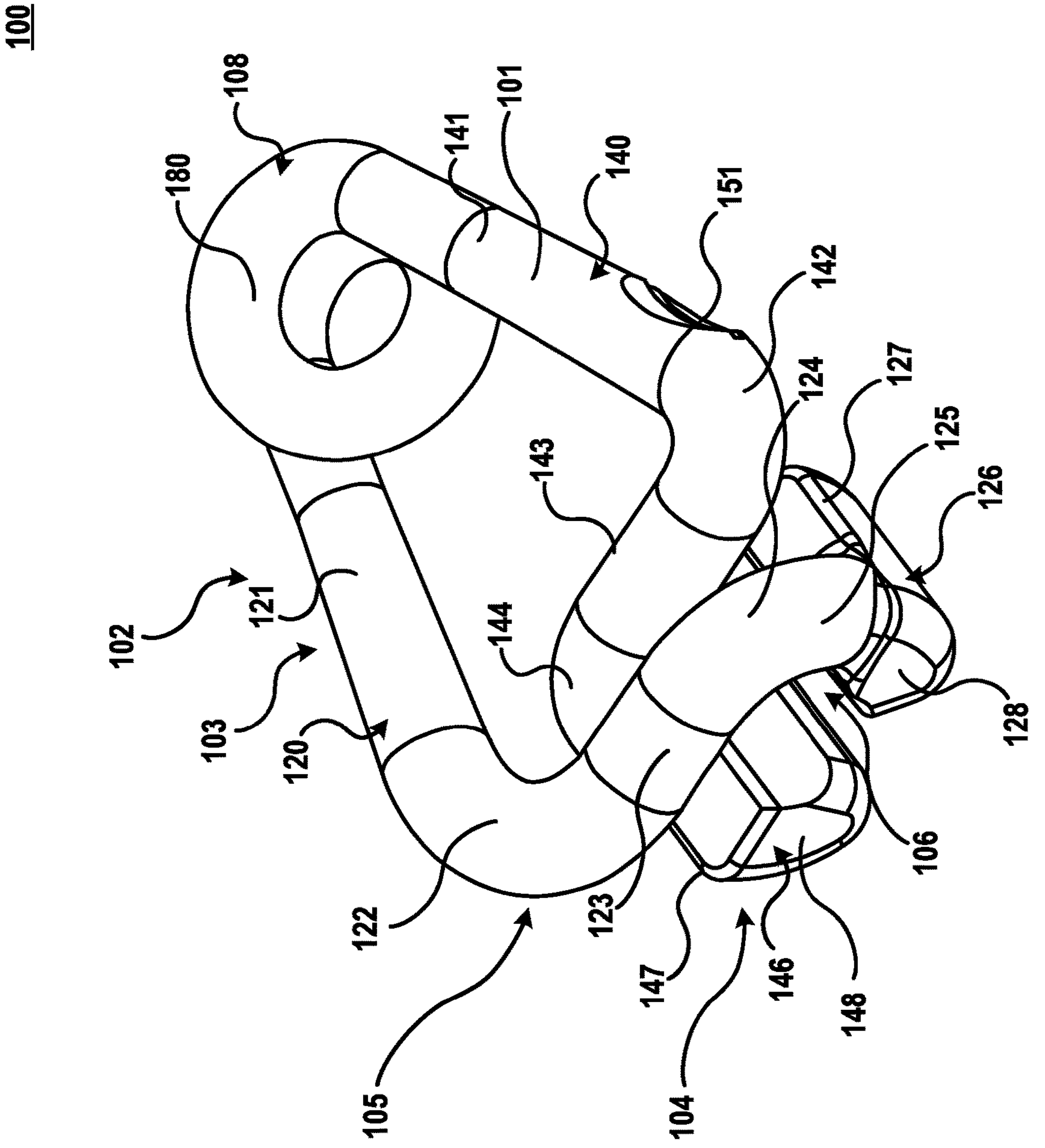
FIG. 2A is an illustration showing a front perspective view of the catheter clip of FIG. 1A.
Figure 2B:
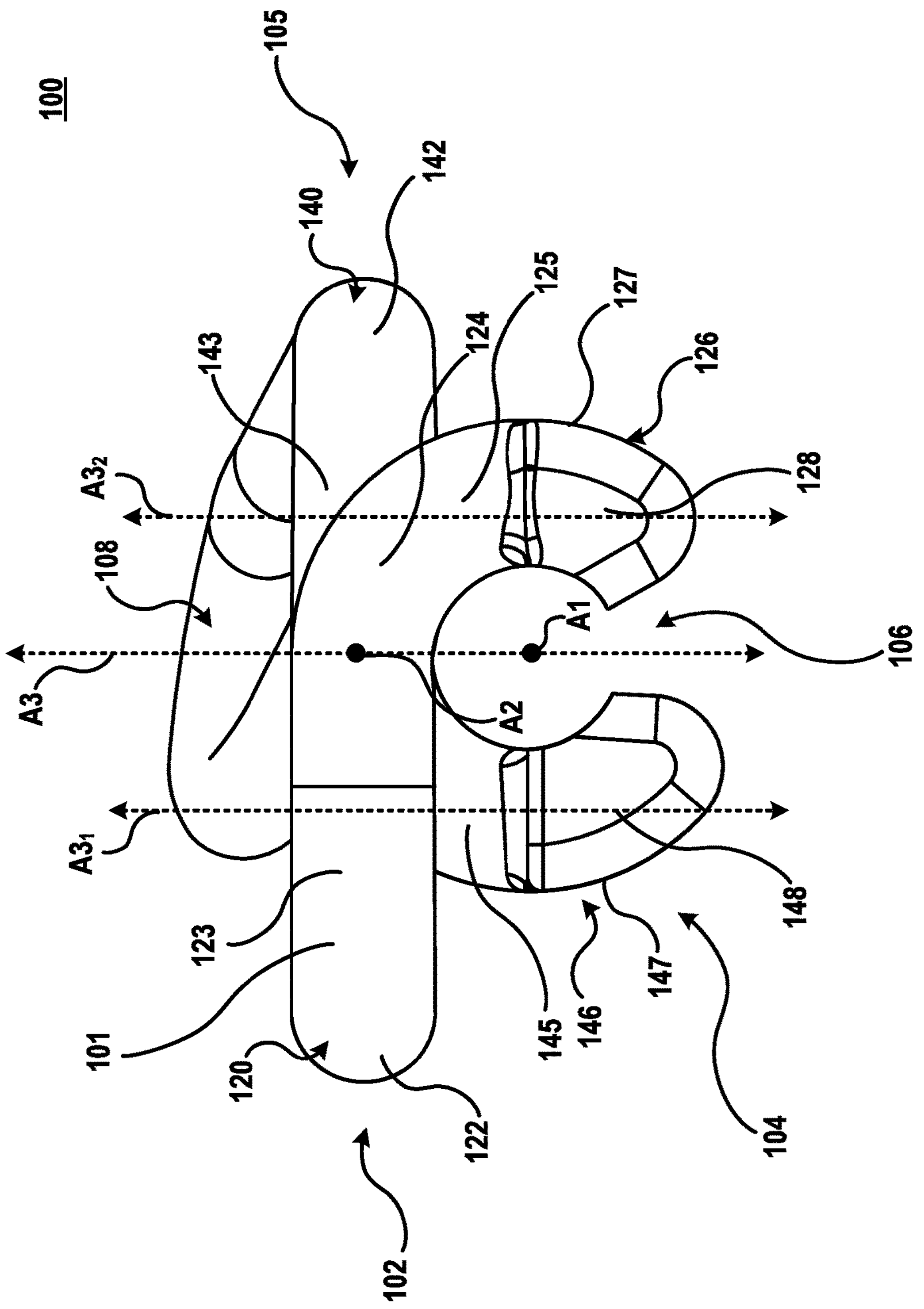
FIG. 2B is an illustration showing a front view of the catheter clip of FIG. 2A.
Figure 2C:
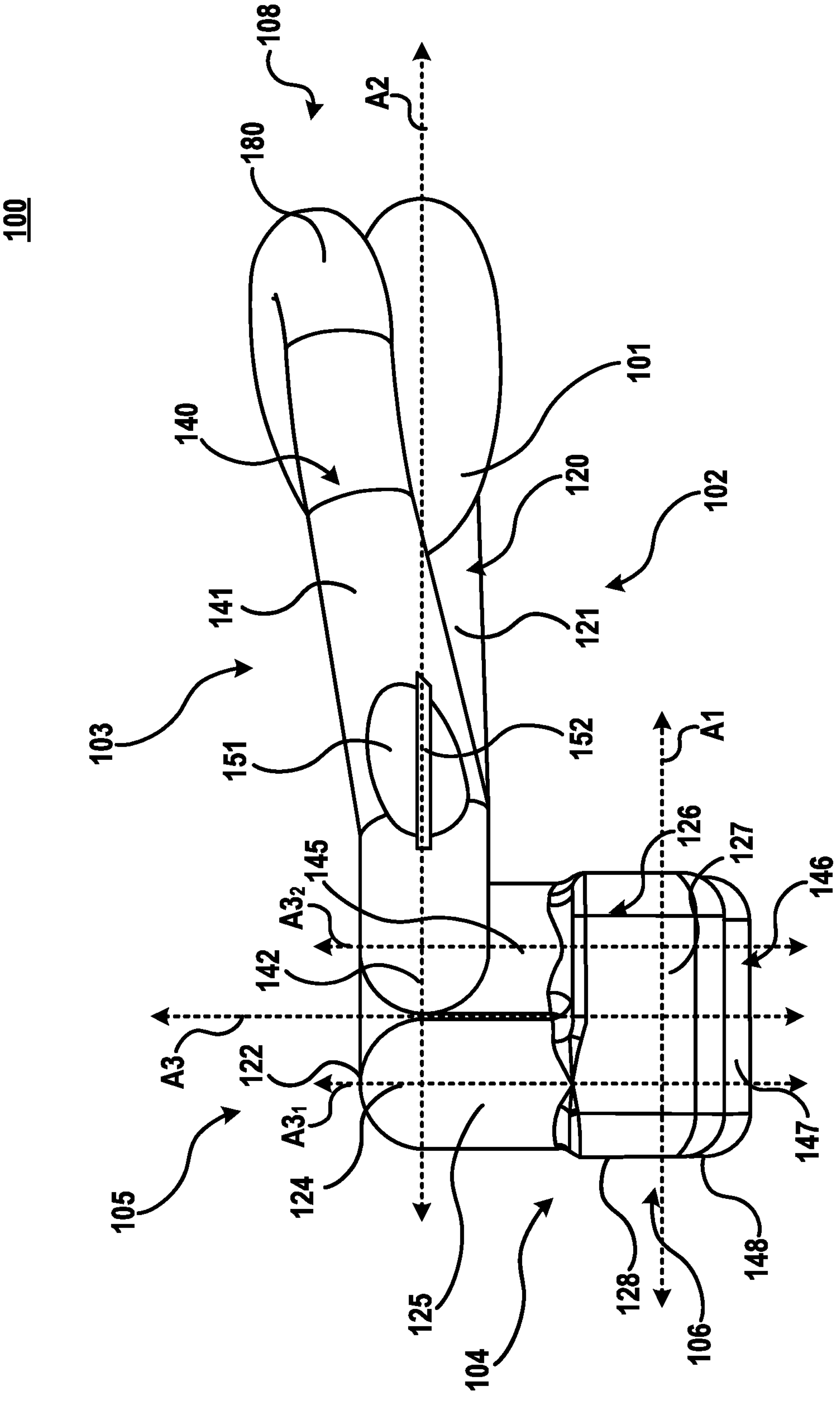
FIG. 2C is an illustration showing a side view of the catheter clip of FIG. 2A.
Figure 2D:
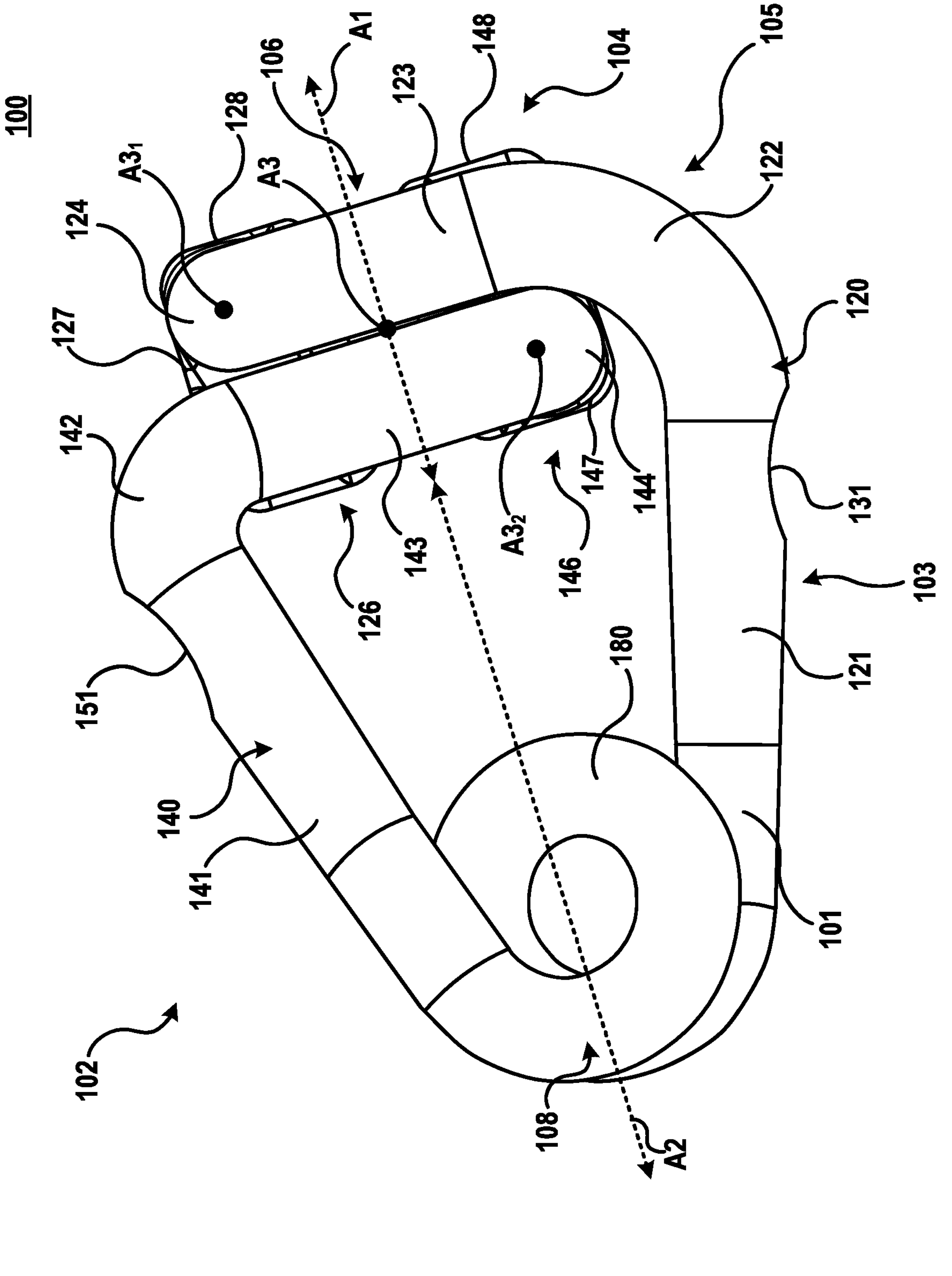
FIG. 2D is an illustration showing a top plan view of the catheter clip of FIG. 2A.
Figure 2E:
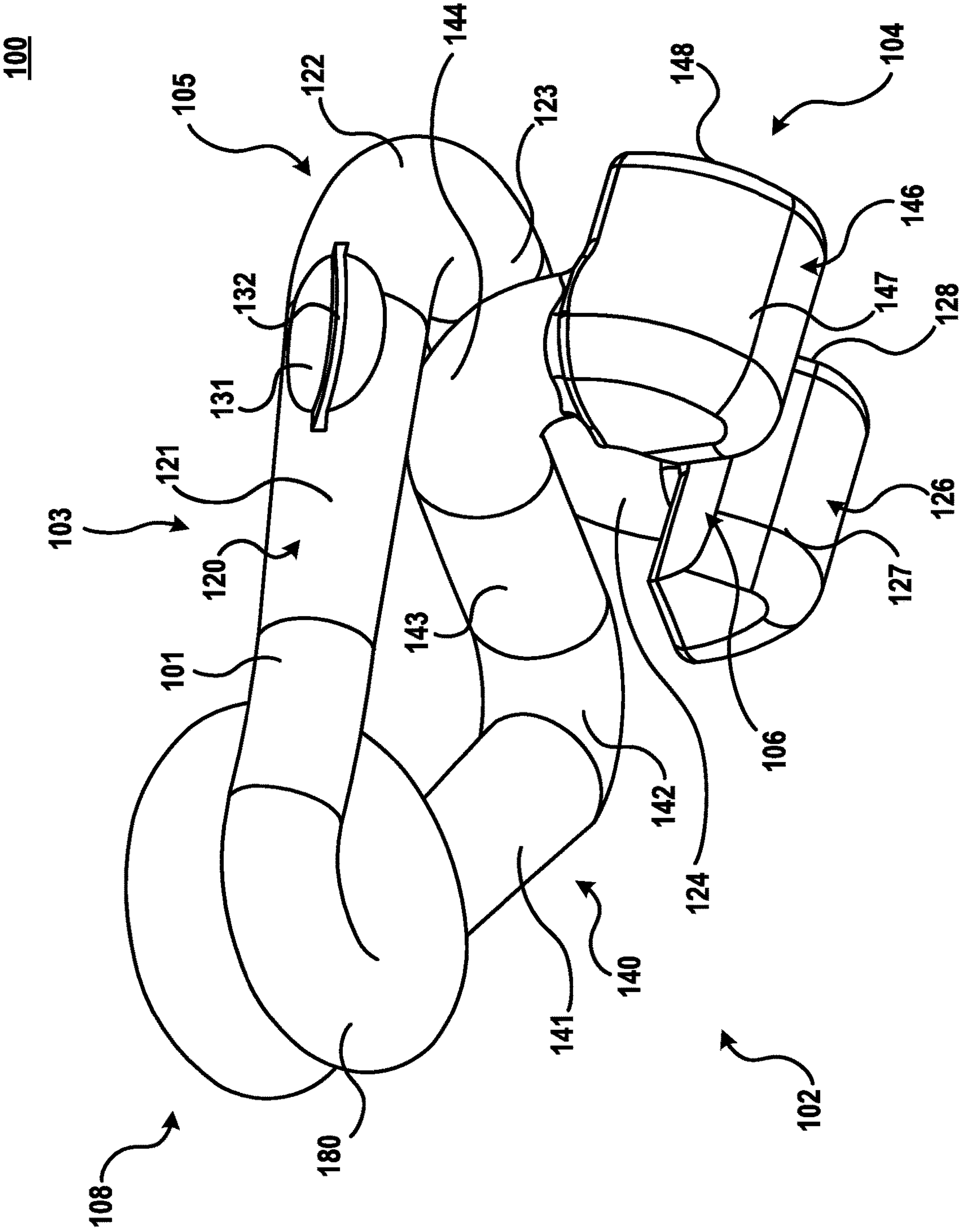
FIG. 2E is an illustration showing a below perspective view of the catheter clip of FIG. 2A.
Figure 2F:
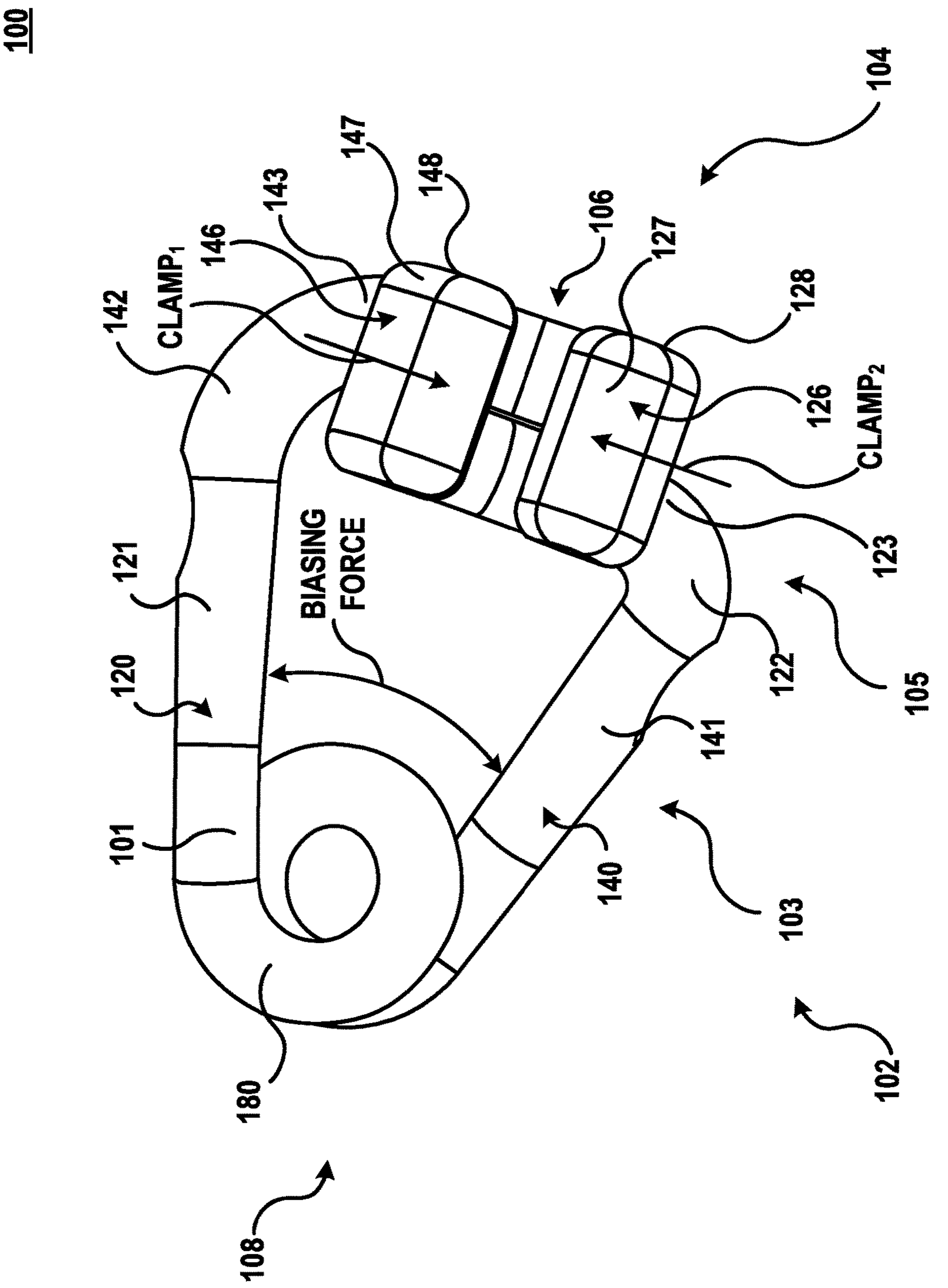
FIG. 2F is an illustration showing a below plan view of the catheter clip of FIG. 2A.

Further, as shown in FIG. 2B, the first terminal portion 125 and the second terminal portion 145 can each define opposing curvatures such that the elongated clamping receptacle 106 formed collectively at the first terminal portion 125 and the second terminal portion 145 has a circular cross-section. The first terminal portion 125 defines the first clamping element 126 that forms a first half of the elongated clamping receptacle 106 and the second terminal portion 145 defines the second clamping element 146 that forms a second half of the elongated clamping receptacle 106. As such, with additional reference to FIGS. 1E, 1F and 2F, the first clamping element 126 applies a first component $CLAMP_1$ of the clamping force and the second clamping element 146 applies a second component $CLAMP_2$ of the clamping force at the elongated clamping receptacle 106, where the first component $CLAMP_1$ and the second component $CLAMP_2$ collectively define the circumferential clamping force applied around the circumference of the catheter 14. The clamping force applied around the catheter 14 is resultant of the first and second components of the biasing forces (e.g., $BIAS_1$ and $BIAS_2$ generated at the tensioning portion 108 which are inverted into the first and second components clamping forces (e.g., $CLAMP_1$ and $CLAMP_2$) at the crossed portion 105.

The first clamping element 126 and the second clamping element 146 of the elongated clamping receptacle 106 define the receptacle axis A1 that extends along the catheter axis $AXIS_C$ (FIG. 1C) to capture the catheter 14. As shown, the first clamping element 126 and the second clamping element 146 extend beyond the first terminal portion 125 and the second terminal portion 145 to maximize a surface area of the catheter 14 that can be captured at the elongated clamping receptacle 106. As shown, the first terminal portion 125 defines a first elongated tab portion 127 that forms a "lower half" of a body of the first clamping element 126 and extends along the receptacle axis A1 to support the catheter 14. Similarly, the second terminal portion 145 defines a second elongated tab portion 147 that forms a "lower half" of a body of the second clamping element 146 and extends along the receptacle axis A1 to support the catheter 14. Because the first lateral portion 123 of the first arm 120 can be positioned farther away from the tensioning portion 108 than the second lateral portion 143 of the second arm 140 as discussed above, the first elongated tab portion 127 can extend in along a first direction of elongation behind the first terminal portion 125 of the first arm 120, whereas the second elongated tab portion 147 can extend in front of the second terminal portion 145 of the second arm 140 in a second direction of elongation that is opposite to the first direction of elongation as shown. While the first elongated tab portion 127 of the first arm 120 and the second elongated tab portion 147 of the second arm 140 extend in opposing directions and the first arm 120 can be slightly longer than the second arm 140, the first elongated tab portion 127 and the second elongated tab portion 147 are equal in length along the receptacle axis A1 to ensure even application of the clamping force at the elongated clamping receptacle 106. The curvatures of the first clamping element 126 (including the first terminal portion 125 and the first elongated tab portion 127) and the second clamping element 146 (including the second terminal portion 145 and the second elongated tab portion 147) of the elongated clamping receptacle 106 ensure that the clamping force is applied circumferentially around the catheter 14.

As further shown in FIGS. 2A-2F, the first elongated tab portion 127 can define a first terminal surface 128 and the second elongated tab portion 147 can define a second terminal surface 148, where both the first terminal surface 128 and the second terminal surface 148 face away from the tensioning portion 108 and are positioned along the same latitude along the clip body 101. When coupled along a shunt valve system 10 as shown in FIGS. 1A-1F, the first terminal surface 128 and the second terminal surface 148 would be positioned closest to the shunt valve 12.

Figure 3C:
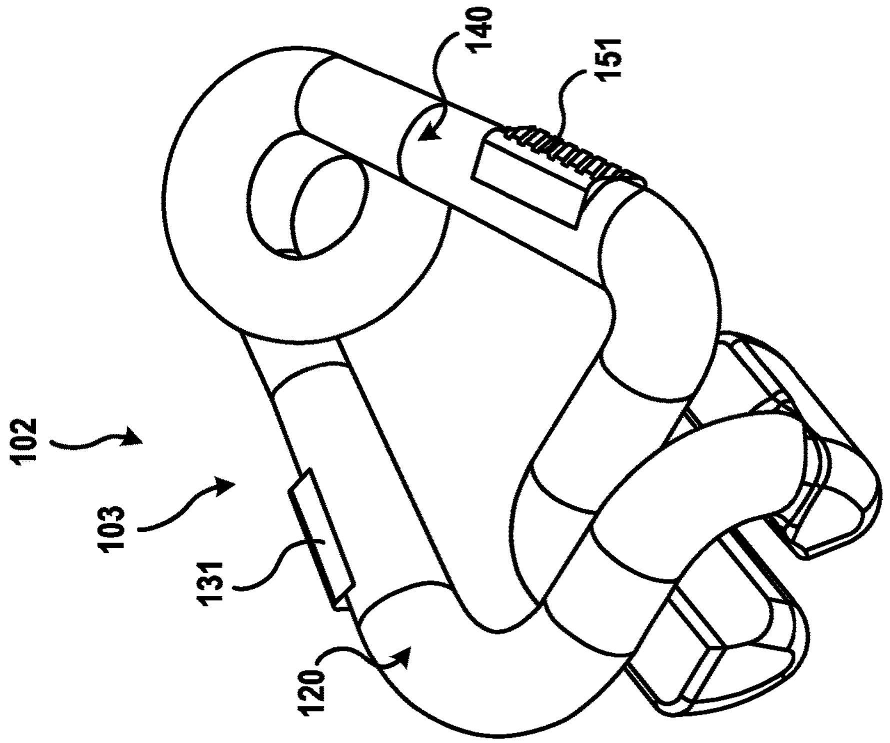
FIG. 3C is an illustration showing a front perspective view of the catheter clip of FIG. 2A having the gripping portion of FIG. 3B.
Figure 3A:
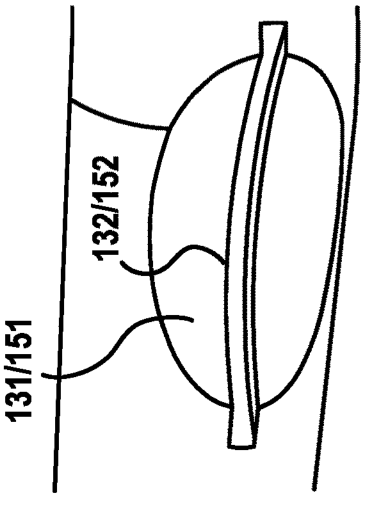
FIGS. 3A and 3B are a pair of illustrations showing options for a gripping portion of the catheter clip of FIG. 2A.
Figure 3B:
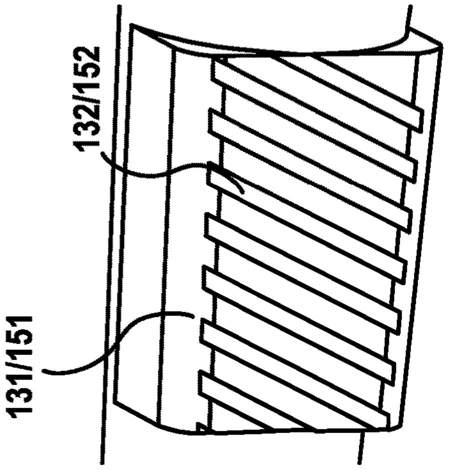

As briefly discussed above, the first arm 120 includes a first gripping portion 131 and the second arm 140 includes a second gripping portion 151 for a practitioner to grip the catheter clip 100 for placement of the catheter clip 100 and to open the elongated clamping receptacle 106. FIGS. 3A and 3B show two possible configurations for the first gripping portion 131 and the second gripping portion 151. In the embodiment of FIG. 3A, the first gripping portion 131 and the second gripping portion 151 are each recess-like grooves along the first arm 120 the first arm 120 and the second arm 140, where the first gripping portion 131 includes a first notch 132 and the second gripping portion 151 includes a second notch 152 for gripping with an applicator. In the embodiment of FIG. 3B, the first gripping portion 131 and the second gripping portion 151 are each block-like structures along the first arm 120 the first arm 120 and the second arm 140, where the first gripping portion 131 includes a first plurality of notches 132 and the second gripping portion 151 includes a second plurality of notches 152 for gripping with an applicator or forceps. FIG. 3C shows an alternate version of the catheter clip 100 having the first gripping portion 131 and the second gripping portion 151 of FIG. 3B.

Figure 4B:
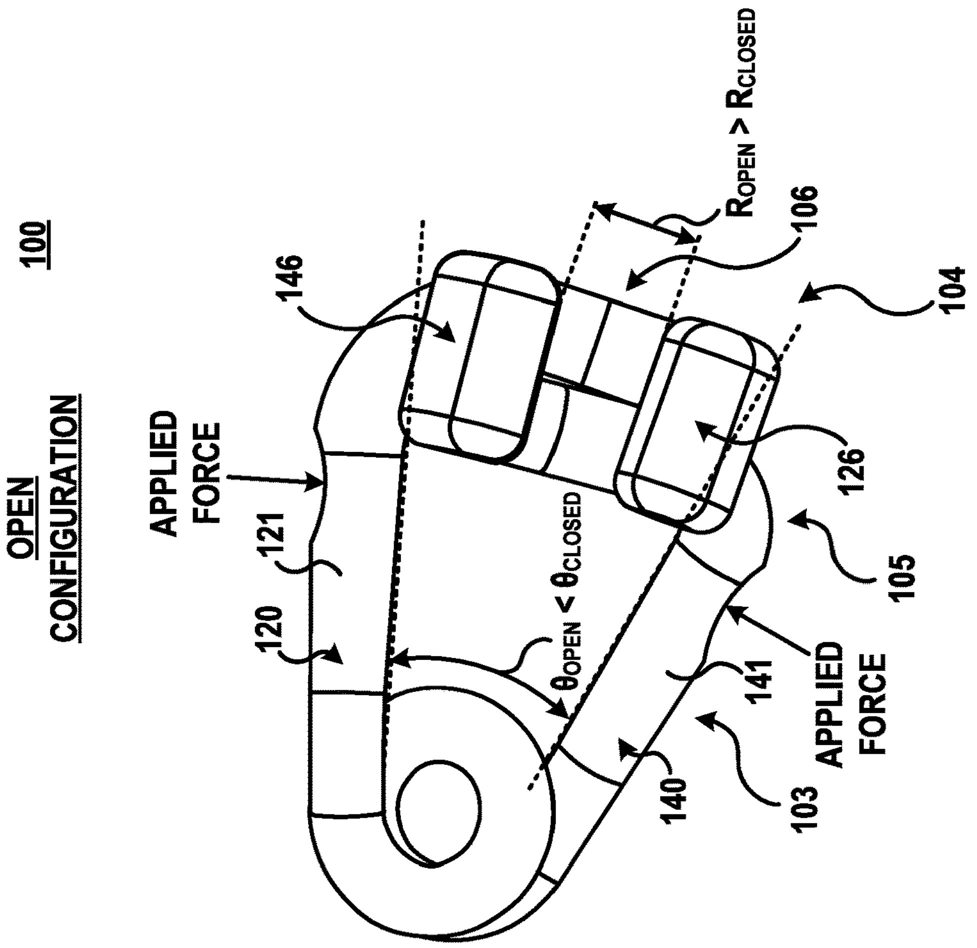
FIGS. 4A and 4B are a pair of illustrations respectively showing below plan views of a first closed configuration and a second open configuration of the catheter clip of FIG. 2A.
Figure 4A:
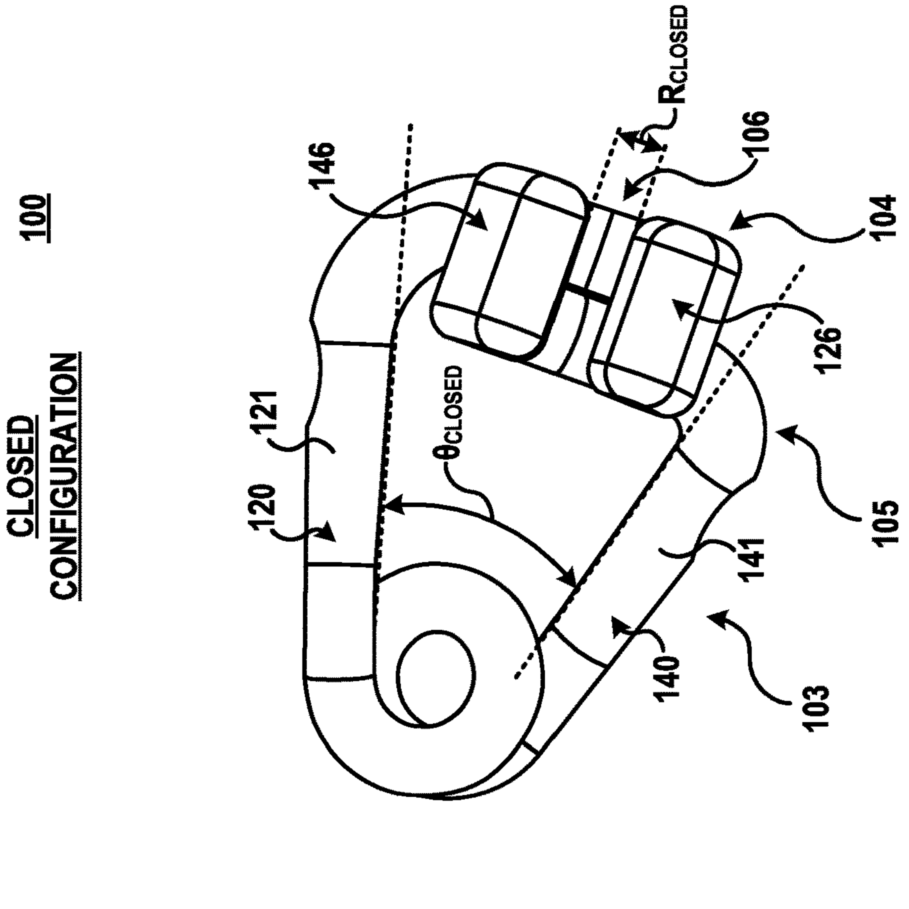
Figure 4C:
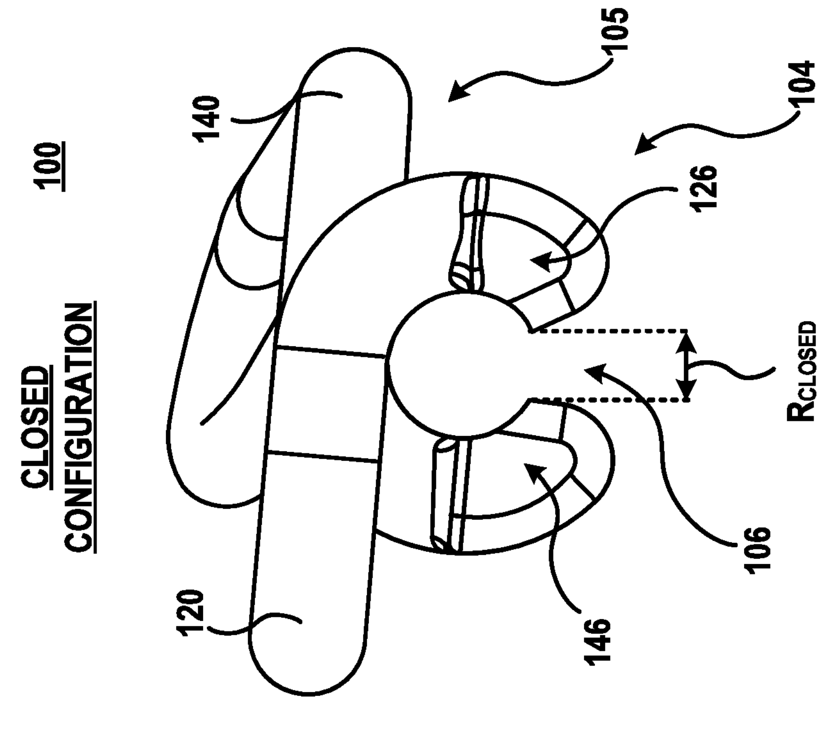
FIGS. 4C and 4D are a pair of illustrations respectively showing front views of a first closed configuration and a second open configuration of the catheter clip of FIG. 2A.
Figure 4D:
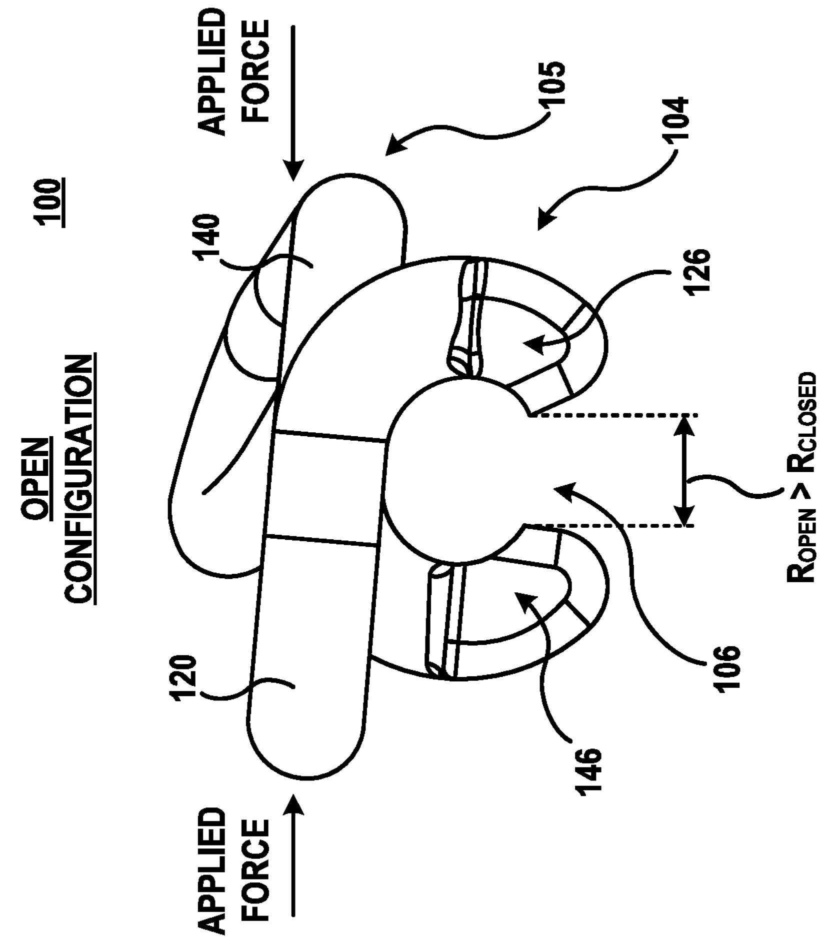

Referring to FIGS. 4A-4D, the catheter clip 100 is operable for assuming a first closed configuration (FIGS. 4A and 4C) or a second open configuration (FIGS. 4B and 4D). In the embodiment shown, the tensioning portion 108 can form a torsion spring arrangement defining a loop 180 between the first arm 120 and the second arm 140. As shown, in the first closed configuration of FIGS. 4A and 4C, the tensioning portion 108 is at rest, defining a "closed" angle @CLOSED and a "closed" distance $D_{CLOSED}$ between the first arm 120 and the second arm 140 and resulting in a closed receptacle width $R_{CLOSED}$ that corresponds with a distance between the first clamping element 126 and the second clamping element 146 of the elongated clamping portion 104. In the closed configuration of FIGS. 4A and 4C, a width of the elongated clamping receptacle 106 is at its smallest. However, as shown in the open configuration of FIGS. 4B and 4D, the first arm 120 and the second arm 140 are compressed together by applied forces along the elongated section 103 of the catheter clip 100 and a torsional force is enacted at the tensioning portion 108, defining an "open" angle $\theta_{OPEN}$ between the first arm 120 and the second arm 140, where the open angle $\theta_{OPEN}$ is less than the closed angle $\theta_{CLOSED}$. In the embodiment shown, for example, the open angle $\theta_{OPEN}$ is 5 degrees smaller than the closed angle $\theta_{CLOSED}$, although the value of the closed angle $\theta_{CLOSED}$ relative to the open angle $\theta_{OPEN}$ can vary based on the amount of force applied at the first arm 120 and the second arm 140. The open angle $\theta_{OPEN}$ results in an open receptacle width $R_{OPEN}$ that corresponds with a distance between the first clamping element 126 and the second clamping element 146 of the elongated clamping portion 104, where the open receptacle width $R_{OPEN}$ is larger than the closed receptacle width $R_{CLOSED}$. Note that due to the crossed portion 105, by compressing the first arm 120 and the second arm 140 together along the elongated section 103 (e.g., by decreasing a distance and an angle between the first longitudinal portion 121 of the first arm 120 and the second longitudinal portion 141 of the second arm 140), the first clamping element 126 of the first arm 120 and the second clamping element 146 of the second arm 140 are forced apart into the "open" configuration.

Figure 5A:
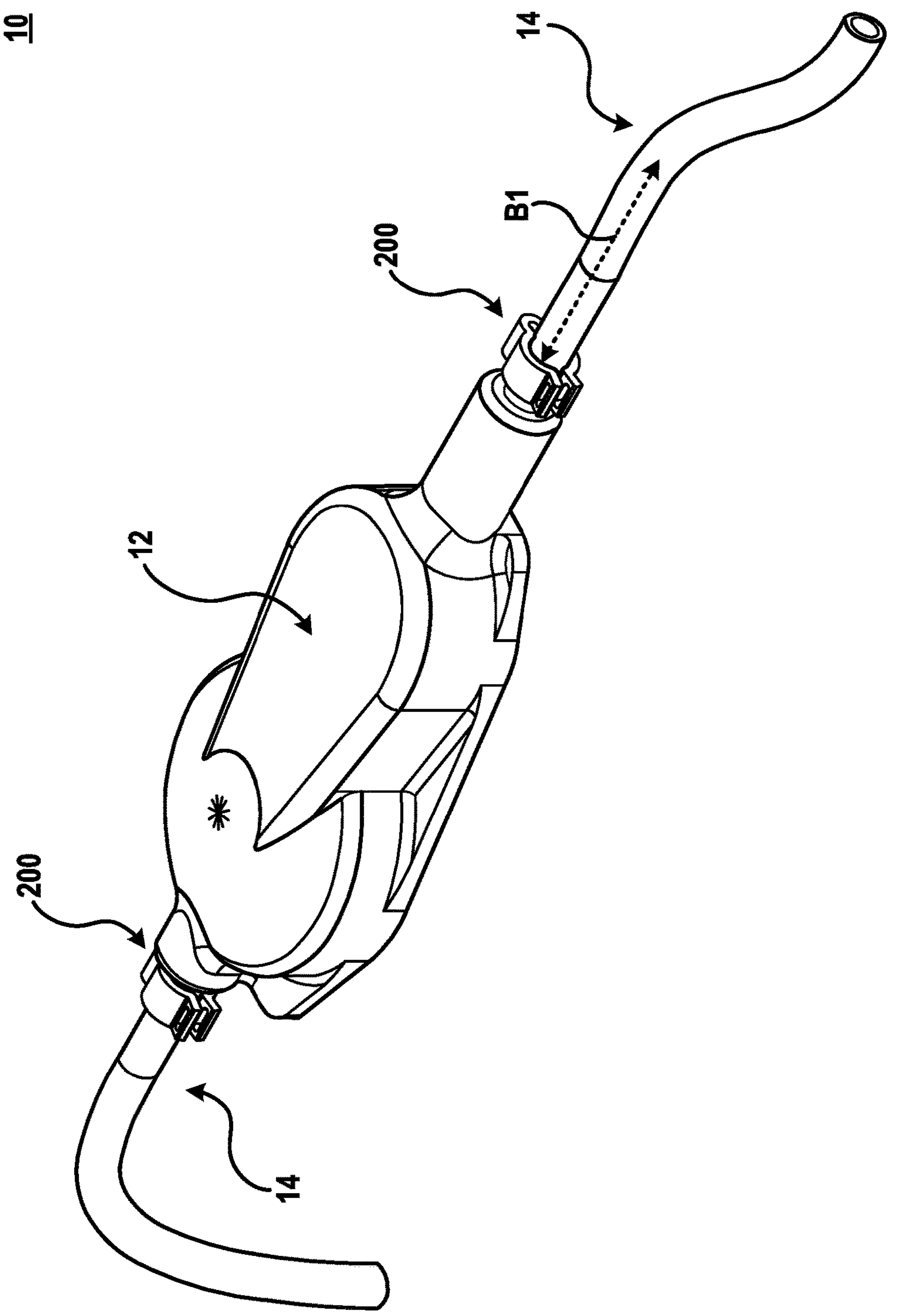
FIG. 5A is an illustration showing a perspective view of a shunt valve system including a second embodiment of a catheter clip.
Figure 5B:
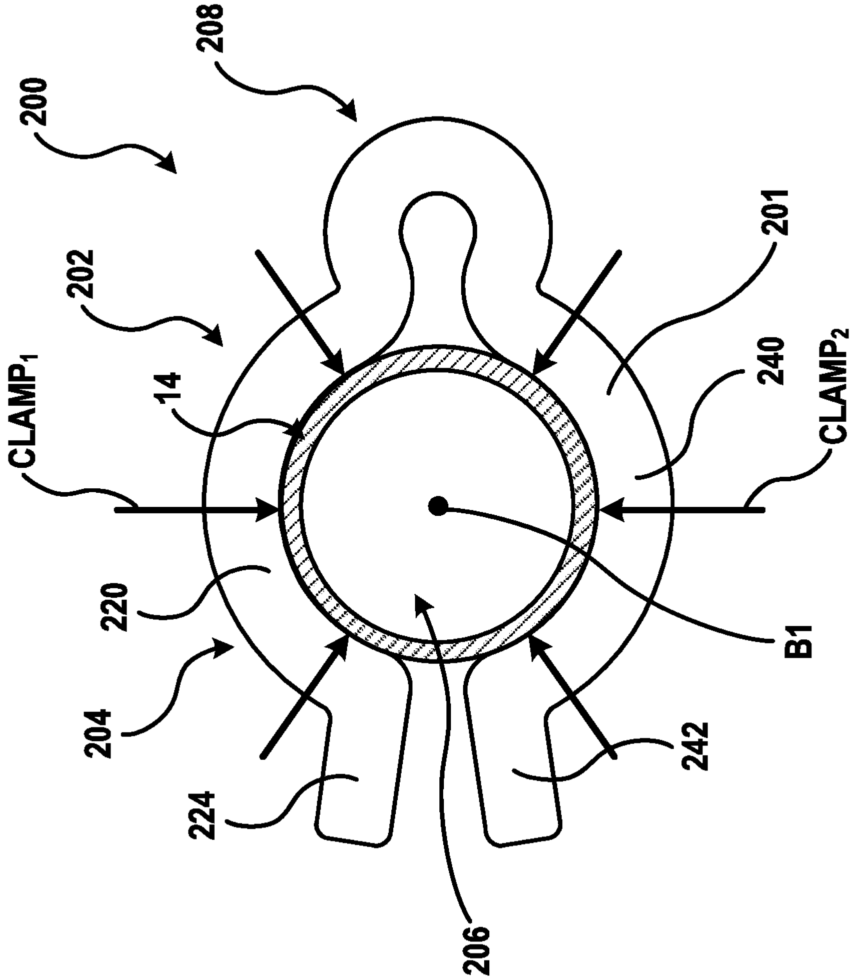
FIG. 5B is an illustration showing the catheter clip of FIG. 5A coupled around a catheter of the shunt valve system.
Figure 6A:
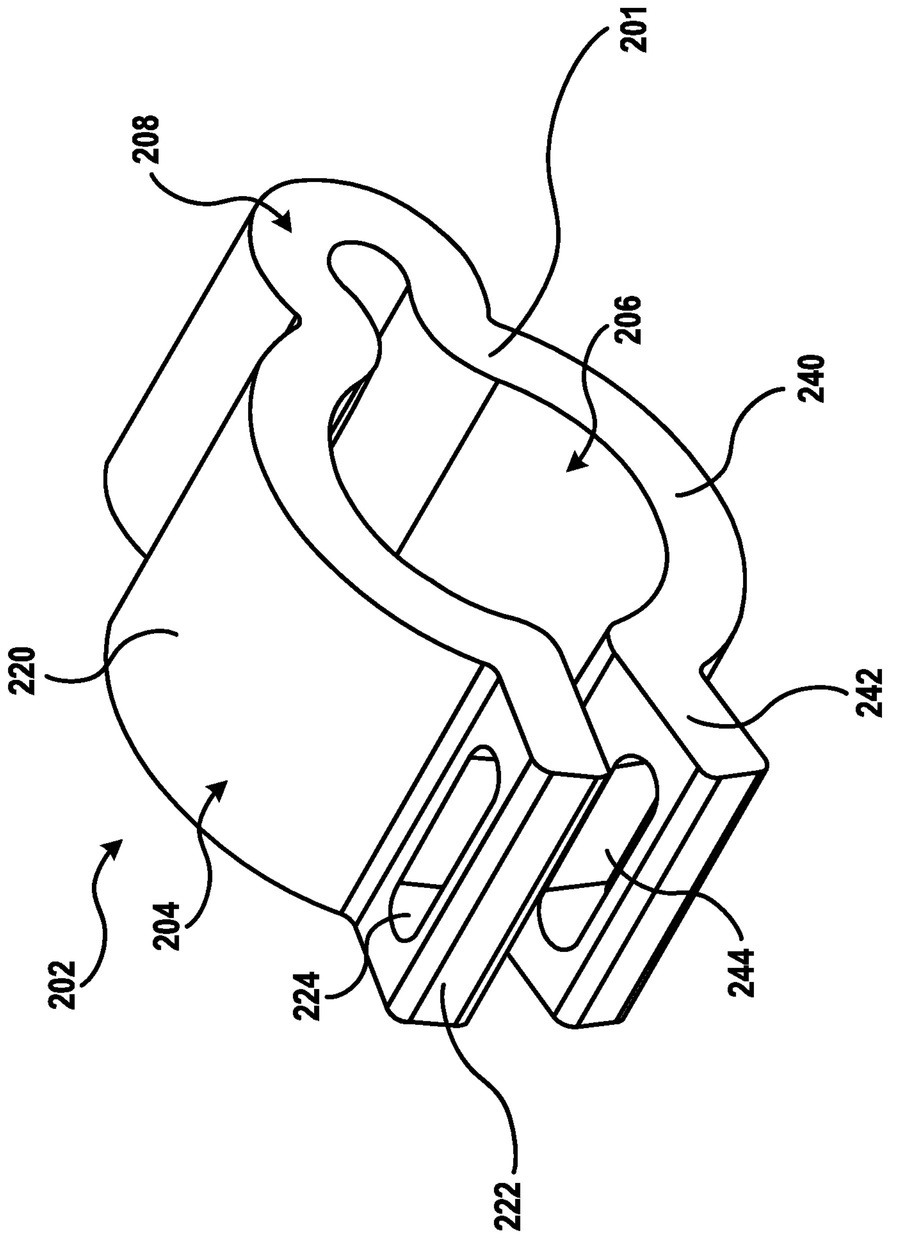
FIG. 6A is an illustration showing a perspective view of the catheter clip of FIG. 5A.
Figure 6B:
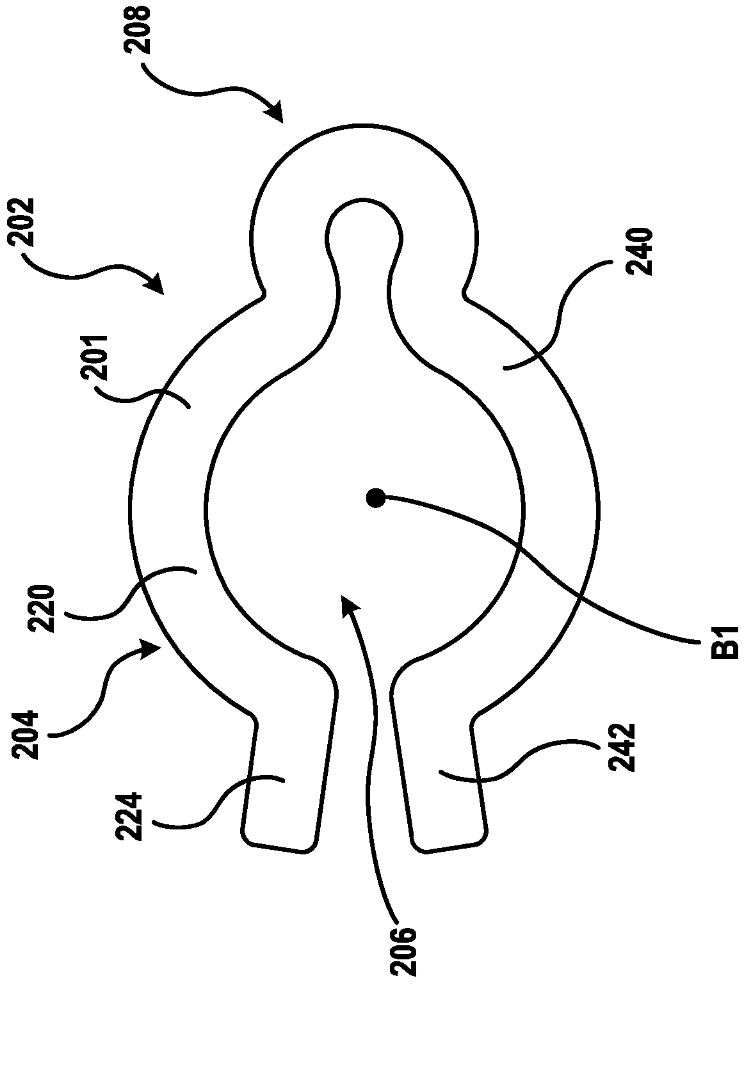
FIG. 6B is an illustration showing a front or rear view of the catheter clip of FIG. 6A.

Additional embodiments of the catheter clip 100 are also contemplated that further simplify the profile of the catheter clip 100. In a second embodiment shown in FIGS. 5A-6B, a catheter clip 200 defines a clip body 201 having a tensioning portion 208 that applies a clamping force around the catheter 14 (FIGS. 5A and 5B); similarly, the clip body 201 can be of a single member. In particular, FIGS. 5A and 5B show the catheter clip 200 coupled with the shunt valve system 10, and FIGS. 6A and 6B show the catheter clip 300 alone. The clip body 201 includes a pair of arms 202 including a first arm 220 and a second arm 240; the first arm 220 and the second arm 240 can be connected at the tensioning portion 208 and can collectively form an elongated clamping portion 204 defining an elongated clamping receptacle 206 along the first arm 220 and the second arm 240 for receipt of the catheter 14. The elongated clamping portion 204 covers a larger surface area along the catheter 14 than sutures, which are used in present shunt valve systems. The clamping force (collectively, a first component $CLAMP_1$ applied by the first arm 220 and a second component $CLAMP_2$ applied by the second arm 240) is a consistent circumferential force to ensure that the catheter 14 is appropriately secured within the elongated clamping receptacle 206. The catheter clip 200 can include a first terminal portion 222 of the first arm 220 and a second terminal portion 242 of the second arm 240 that enable a practitioner to grasp the catheter clip 200 with an applicator or standard forceps.

As shown, the elongated clamping receptacle 206 defines a receptacle axis B1 that aligns with a direction of elongation of the catheter 14 when the catheter 14 is captured therein. The first arm 220 applies a first component $CLAMP_1$ of the clamping force and the second arm 240 applies a second component $CLAMP_2$ of the clamping force to the catheter 14, where the first component $CLAMP_1$ and the second component $CLAMP_2$ collectively define the circumferential clamping force applied around the circumference of the catheter 14. The first arm 220 and the second arm 240 both define a curvature along the elongated clamping portion 204 such that the elongated clamping receptacle 206 defined therebetween has a circular cross-section; this curvature ensures that the clamping force is applied circumferentially around the catheter 14.

As shown, the first terminal portion 222 includes a first slot 224 and the second terminal portion 242 includes a second slot 244. The first slot 224 and the second slot 244 can enable a practitioner to grasp the catheter clip 200 with an applicator or standard forceps, separate the first terminal portion 222 and the second terminal portion 242 from one another such that the practitioner can insert the catheter 14 into the elongated clamping receptacle 206, and then draw the first terminal portion 222 and the second terminal portion 242 together. Note that in this embodiment, the first terminal portion 222 and the second terminal portion 242 do not necessarily need to couple with one another in a securing arrangement, although it is possible for the catheter clip 200 to be configured to couple with one another in a securing arrangement.

Figure 7A:
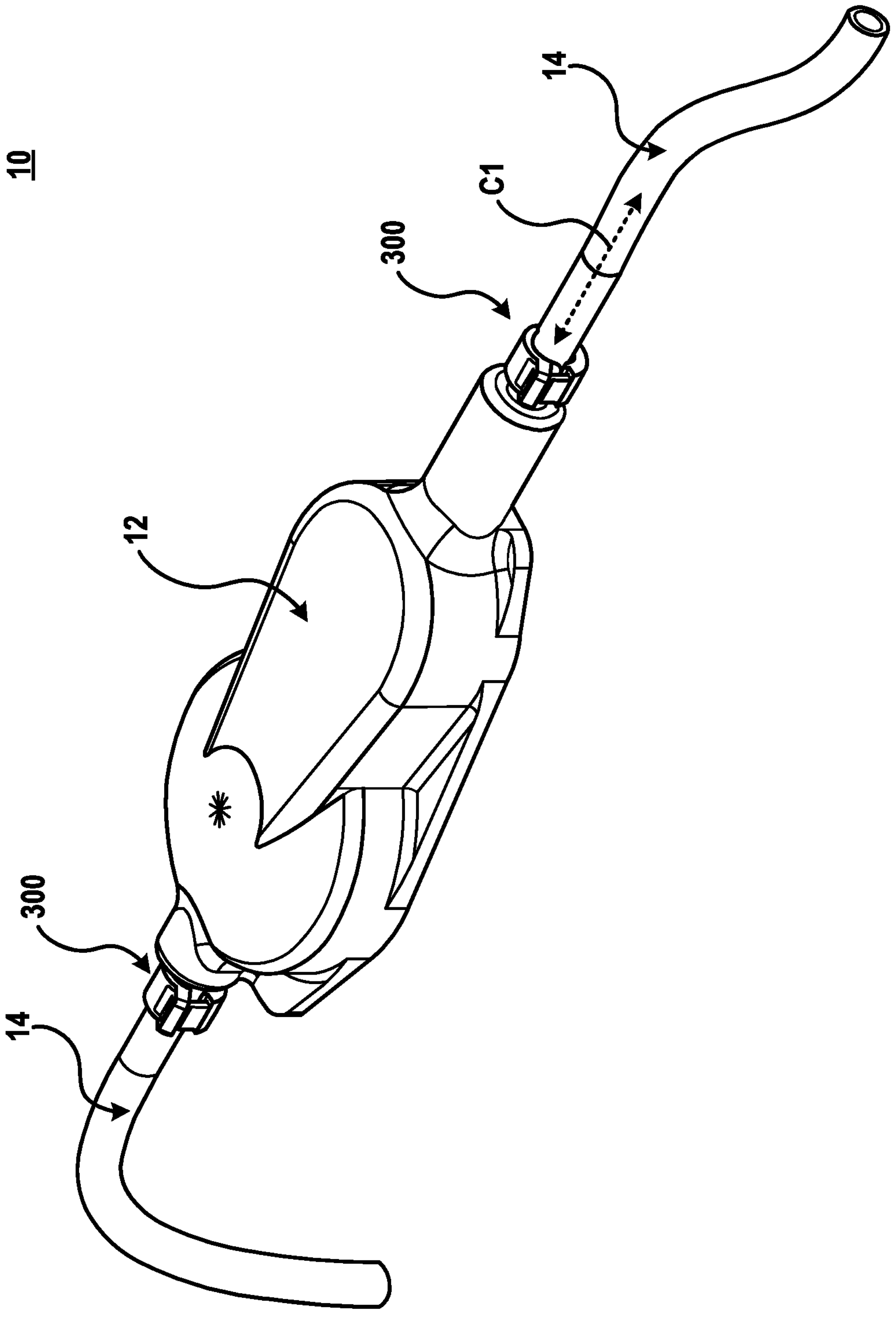
FIG. 7A is an illustration showing a perspective view of a shunt valve system including a third embodiment of a catheter clip.
Figure 7B:
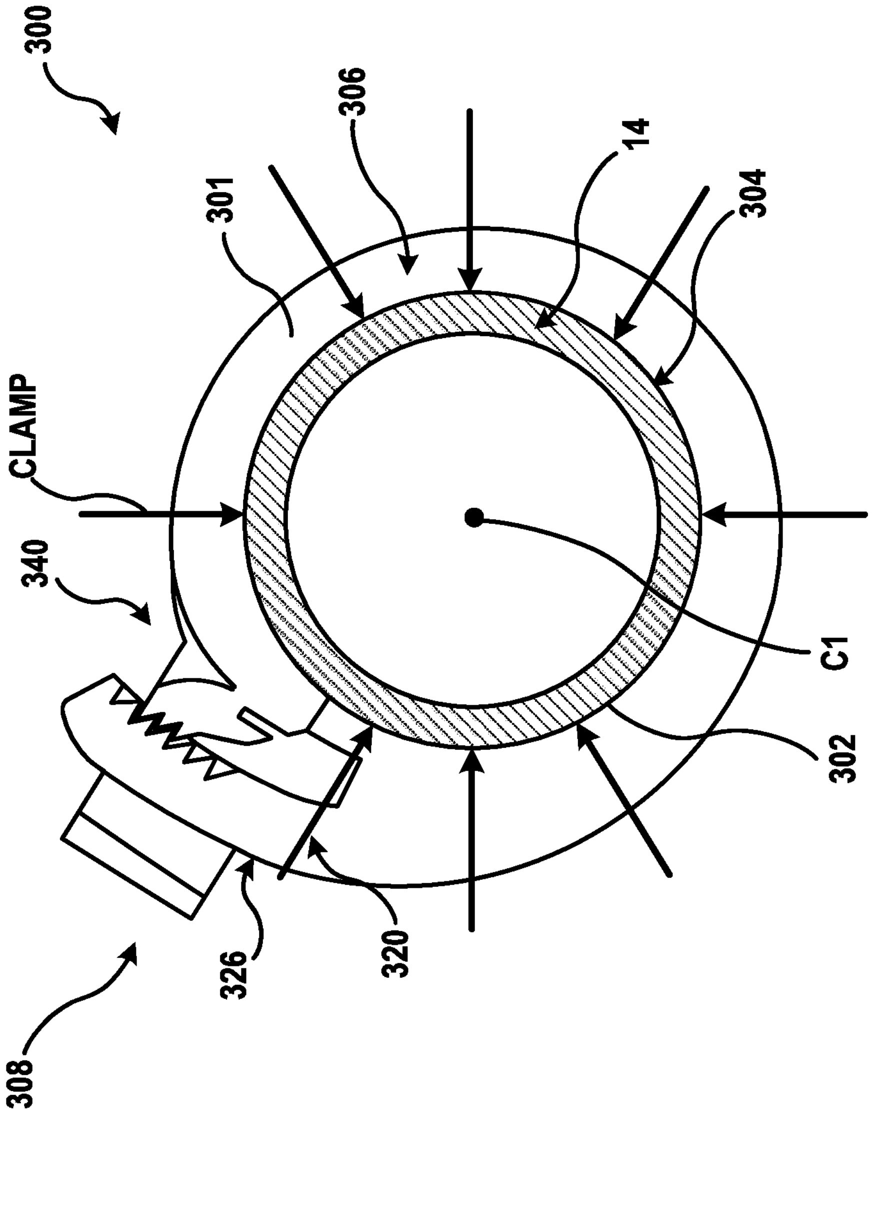
FIG. 7B is an illustration showing the catheter clip of FIG. 7A coupled around a catheter of the shunt valve system.
Figure 8A:
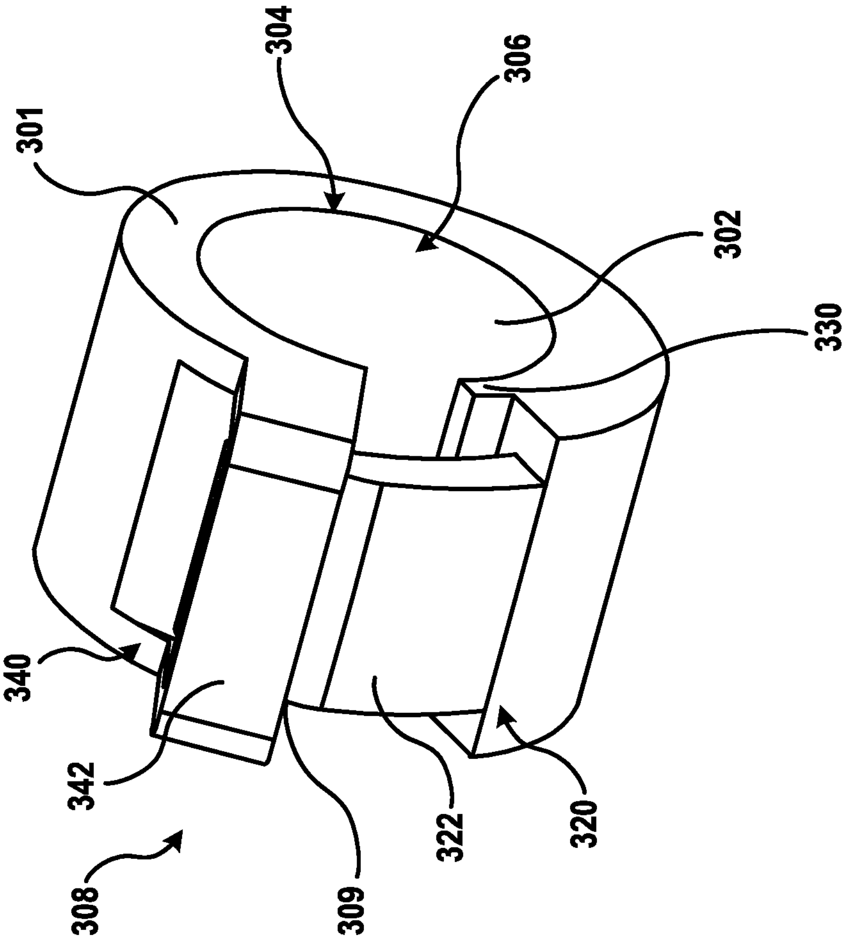
FIG. 8A is an illustration showing a perspective view the catheter clip of FIG. 7A.
Figure 8C:
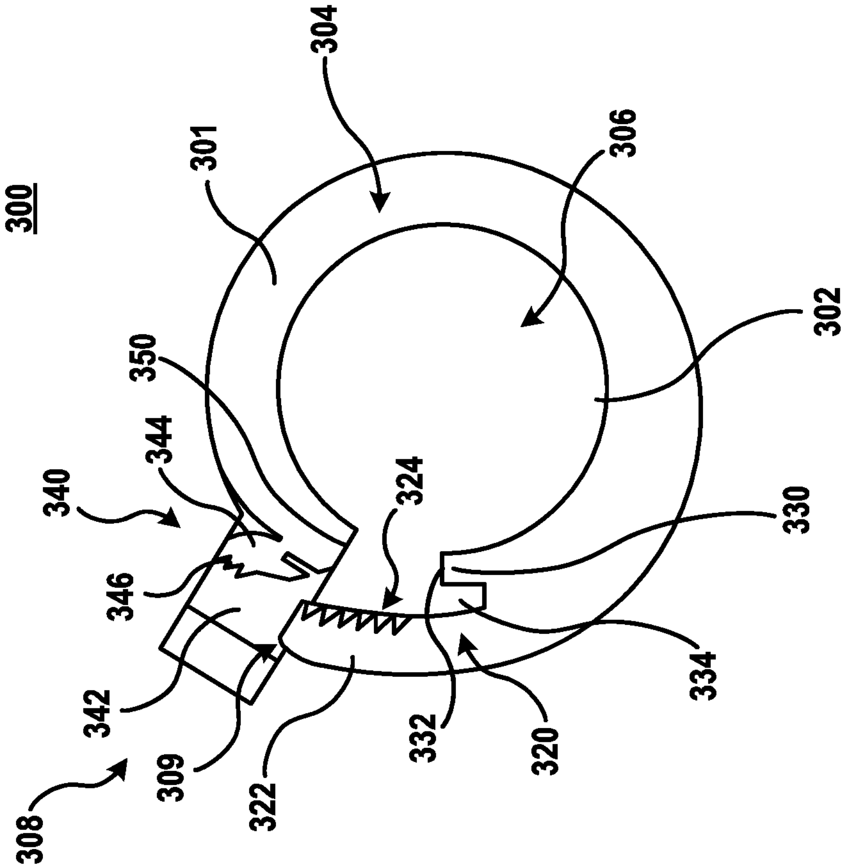
FIG. 8C is an illustration showing a cross-sectional view of the catheter clip of FIG. 8B in the decoupled state (e.g., the second open configuration)
Figure 8B:
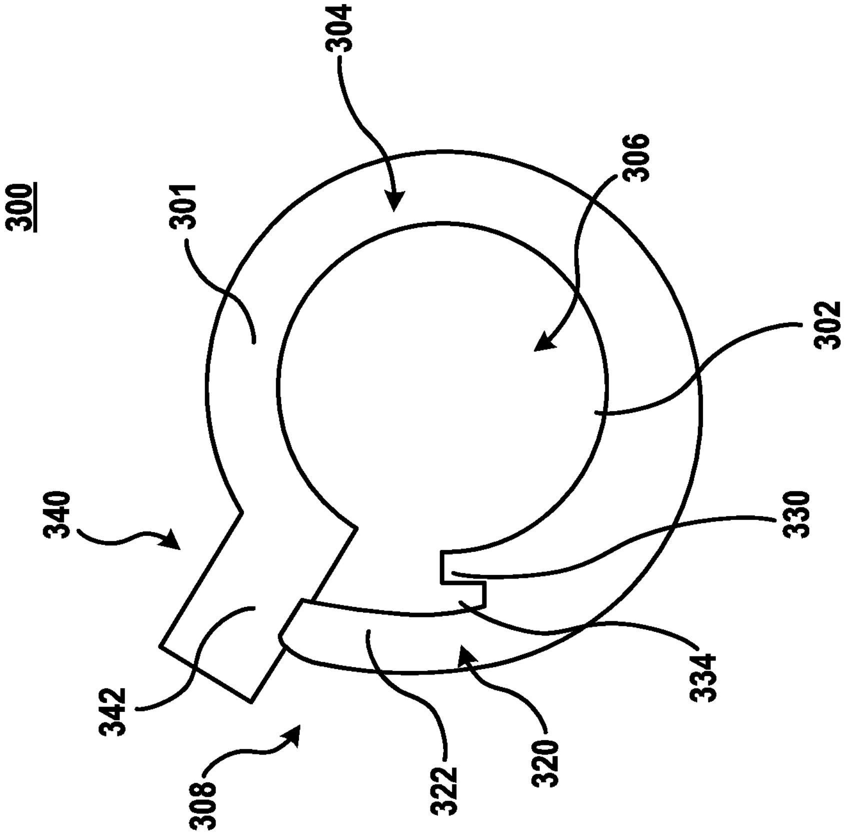
FIG. 8B is an illustration showing a front or rear view of the catheter clip of FIG. 8A in a decoupled state (e.g., a second open configuration)
Figure 8E:
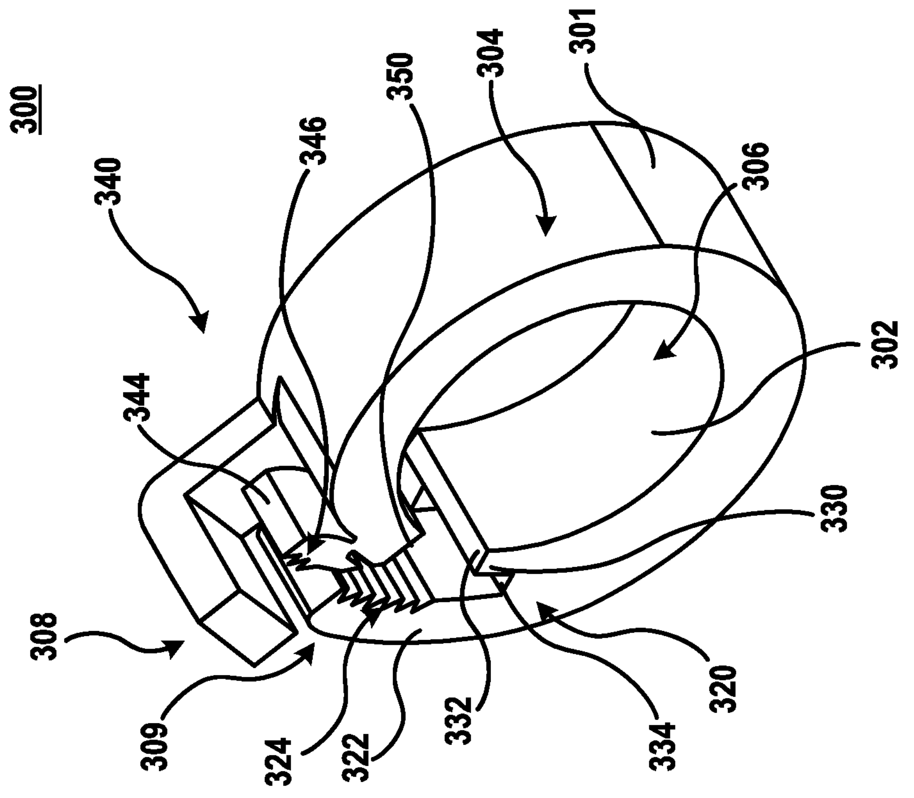
FIG. 8E is an illustration showing a cross-sectional perspective view of the catheter clip of FIG. 8D in the decoupled state (e.g., the second open configuration)
Figure 8D:
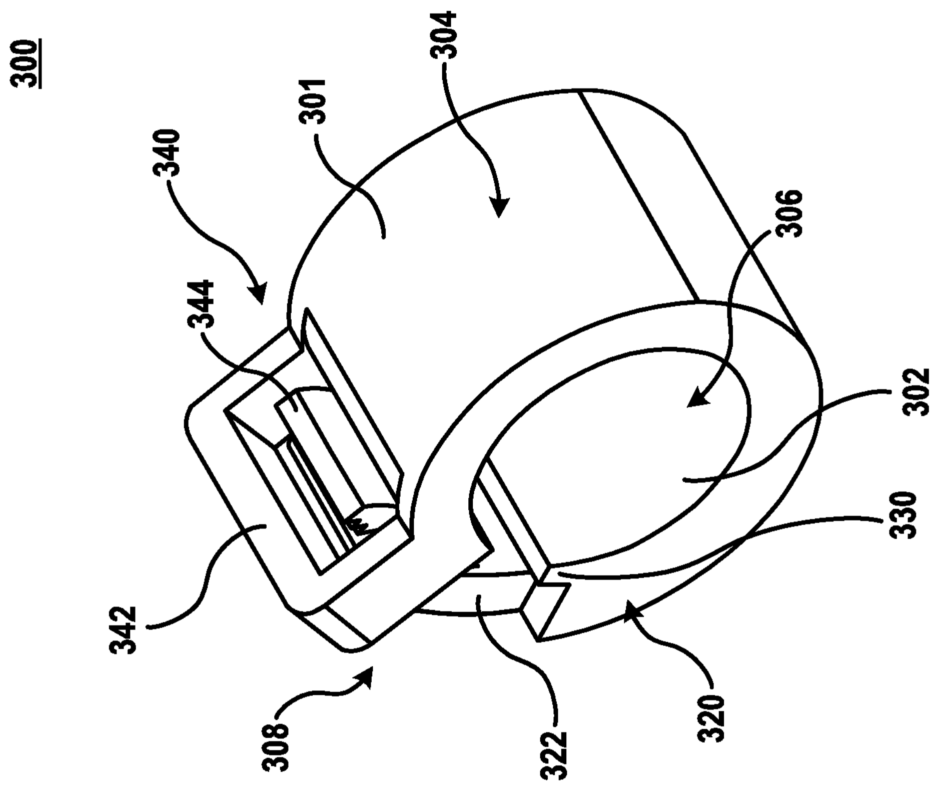
FIG. 8D is an illustration showing a perspective view of the catheter clip of FIG. 8A in a decoupled state (e.g., a second open configuration)
Figure 8F:
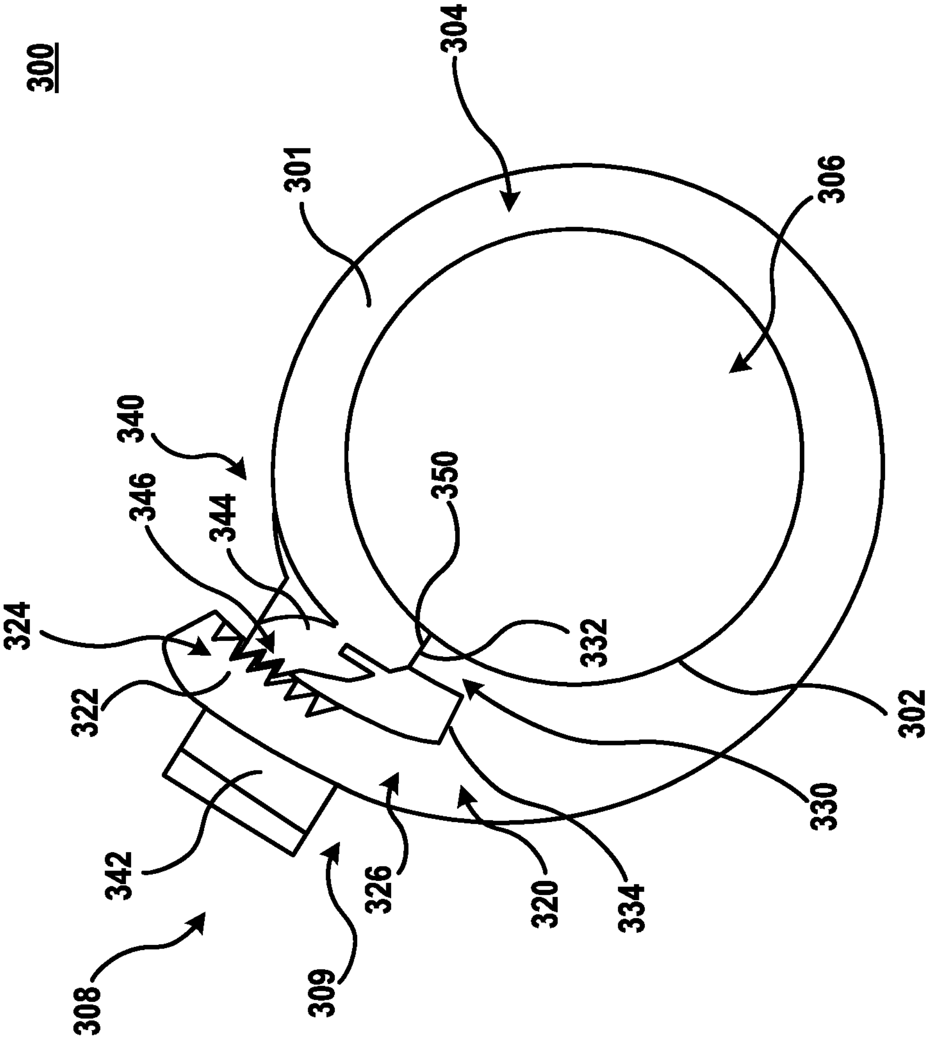
FIG. 8F is an illustration showing a cross-sectional perspective view of the catheter clip of FIG. 8D in a coupled state (e.g., a first closed configuration)

In a third embodiment shown in FIGS. 7A-8F, a catheter clip 300 similarly defines a clip body 301 having a tensioning portion 308 that applies a clamping force CLAMP around the catheter 14 of the shunt valve system 10. In particular, FIGS. 7A and 7B show the catheter clip 300 coupled with the shunt valve system 10, FIGS. 8A-8F show the catheter clip 300 alone, where FIGS. 8A, 8B, and 8D show various views of the catheter clip 300 in a second "open" configuration, FIGS. 8C and 8E show cross-sectional views of the catheter clip 300 in the second "open" configuration, and FIG. 8F shows a cross-sectional view of the catheter clip 300 in a first "closed" configuration. In this embodiment, the clip body 301 can similarly be of a single member forming an elongated clamping portion 304 defining an elongated clamping receptacle 306 along an interior-facing surface 302 of the clip body 301 for receipt of the catheter 14; the elongated clamping receptacle 306 similarly defines a receptacle axis C1 that aligns with a direction of elongation of the catheter 14 when the catheter 14 is captured therein. The elongated clamping portion 304 covers a larger surface area along the catheter 14 than sutures, which are used in present shunt valve systems. The tensioning portion 308 can be defined at a junction 309 of a first terminal portion 320 of the clip body 301 and a second terminal portion 340 of the clip body 301 and can serve a dual purpose of generating the clamping force and securing the catheter clip 300 around the catheter 14 in a securing arrangement when the first terminal portion 320 and the second terminal portion 340 are coupled with one another. The clamping force applied at the elongated clamping receptacle 306 is a consistent circumferential force to ensure that the catheter 14 is appropriately secured. The tensioning portion 308 can include a ratchet arrangement to incrementally increase the clamping force applied at the elongated clamping receptacle 306 and prevent de-tensioning of the catheter clip 300.

As shown, the tensioning portion 308 is defined at the junction 309 of the first terminal portion 320 and the second terminal portion 340 of the clip body 301. FIGS. 8A-8E show the catheter clip 300 with the first terminal portion 320 and the second terminal portion 340 decoupled from one another, and FIG. 8F shows the catheter clip 300 with the first terminal portion 320 and the second terminal portion 340 coupled at the tensioning portion 308. The first terminal portion 320 can include a ratchet protrusion 322 having a plurality of ratchet teeth 324, and the second terminal portion 340 can include a ratchet receptacle 342 configured to receive the ratchet protrusion 322; the ratchet receptacle 342 includes a tongue protrusion 344 having one or more receiving teeth 346 for incremental engagement with one or more of the plurality of ratchet teeth 324. As the ratchet protrusion 322 advances through the ratchet receptacle 342, the first terminal portion 320 and the second terminal portion 340 are drawn together and the diameter of the elongated clamping receptacle 306 is reduced, increasing the clamping force applied at the elongated clamping receptacle 306 when the catheter 14 is captured therein.

As such, to couple the first terminal portion 320 and the second terminal portion 340 together at the tensioning portion 308 as shown in FIG. 8F, a practitioner can insert the ratchet protrusion 322 of the first terminal portion 320 into the ratchet receptacle 342 of the second terminal portion 340 such that a ratchet tooth 324 of the plurality of ratchet teeth 324 of the ratchet protrusion 322 engages one or more receiving teeth 346 of the tongue protrusion 344 of the ratchet receptacle 342. Following insertion, the practitioner can draw the ratchet protrusion 322 of the first terminal portion 320 through the ratchet receptacle 342 of the second terminal portion 340 until the clamping force applied along the overlap region 18 of the shunt valve system 10 is sufficient as shown in FIG. 7B. In some embodiments, a value of the clamping force can be correlated with a length of a remaining portion 326 of the ratchet protrusion 322 that is not inserted past the tongue protrusion 344 of the ratchet receptacle 342.

As shown, the first terminal portion 320 of the clip body 301 can include a spacer 330 having a terminal spacer surface 332 along the interior-facing surface 302 of the clip body 301 that extends alongside the ratchet protrusion 322, the terminal spacer surface 332 of the spacer 330. The spacer 330 can prevent over-tightening of the catheter clip 300 and resultant prevent over-compression of the catheter 14 by contacting a terminal clip body surface 350 at the second terminal portion 340 of the clip body 301, preventing further advancement of the ratchet protrusion 322 through the ratchet receptacle 342. To de-tension the catheter clip 300, a practitioner can lift the ratchet protrusion 322 away from the tongue protrusion 344 to decouple the ratchet teeth 324 of the ratchet protrusion 322 from the one or more receiving teeth 346 of the tongue protrusion 344.

In another aspect, a length of the spacer 330 can be configured such that the terminal spacer surface 332 contacts the terminal clip body surface 350 before the ratchet protrusion 322 is fully advanced through the ratchet receptacle 342, fixing the minimum width of the elongated clamping receptacle 306. If a diameter of the catheter 14 is smaller, if necessary, a practitioner can cut the spacer 330 to shorten the spacer 330 such that the (new) terminal spacer surface 332 contacts the terminal clip body surface 350 to allow a practitioner to further advance the ratchet protrusion 322 through the ratchet receptacle 342 and reduce the resultant width of the elongated clamping receptacle 306. The spacer 330 can include an intermediate space 334 between the ratchet protrusion 322 and the spacer 330 that provides a space for scissors or another cutting tool so that a practitioner can cut the ratchet protrusion 322 to de-tension and remove the catheter clip 300 from the catheter 14, or so that a practitioner can cut the spacer 330 to a shortened length.

In a fourth embodiment shown in FIGS. 9A-10E, a catheter clip 400 similarly defines a clip body 401 having a tensioning portion 408 that applies a clamping force around the catheter 14 of the shunt valve system 10, where the clamping force is a consistent circumferential force to ensure that the catheter 14 is appropriately secured. In a further aspect, as shown in FIGS. 9A-9G, the catheter clip 400 also applies an additional clamping force around a shunt valve terminal 22 of the shunt valve 12 of the shunt valve system 10 to ensure that the catheter 14 is appropriately secured to the shunt valve 12.

FIGS. 9A-9G show engagement of the catheter clip 400 with the shunt valve system 10, and FIGS. 10A-10E show the catheter clip 400 alone. The clip body 401 of the catheter clip 400 includes a first elongated clamping portion 404 having a first elongated clamping receptacle 406 that captures the overlap portion 18 along the catheter 14, and further includes a second elongated clamping portion 454 having a second elongated clamping receptacle 456 that captures the shunt valve terminal 22 of the shunt valve 12. The clip body 401 also defines a tensioning portion 408 that generates the clamping force applied at the first elongated clamping portion 404 and the second elongated clamping portion 454. As shown, the first elongated clamping portion 404 and the second elongated clamping portion 454 collectively define a receptacle axis D1 that aligns with the catheter axis $AXIS_C$, and the tensioning portion 408 defines an upper line D2 that is parallel to the receptacle axis D1 as shown. As shown, the first elongated clamping receptacle 406 and the second elongated clamping receptacle 456 each define a circular cross-section.

As shown, the first elongated clamping portion 404 can include a first forward arm 420 having a first forward terminal portion 422 and a second forward arm 430 having a second forward terminal portion 432 that collectively define the first elongated clamping receptacle 406 therebetween. A direction of elongation collectively defined by the first forward arm 420 and the second forward arm 430 of the first elongated clamping portion 404 is denoted by a first vertical line $D3_1$, where the first vertical line $D3_1$ is perpendicular to the receptacle axis D1 and the upper line D2. The first forward arm 420 and the second forward arm 430 collectively apply the clamping force around the catheter 14; in particular, the first forward arm 420 applies a first component $CLAMP_1$ (FIG. 9D) of the clamping force and the second forward arm 430 applies a second component $CLAMP_2$ (FIG. 9D) of the clamping force to the catheter 14 when the catheter 14 is captured at the first elongated clamping receptacle 406, where the first component $CLAMP_1$ and the second component $CLAMP_2$ collectively define the consistent circumferential force applied around the catheter 14. The first elongated clamping portion 404 defines a first opening 405 between the first forward terminal portion 422 of the first forward arm 420 and the second forward terminal portion 432 of the second forward arm 430 that communicates with the first elongated clamping receptacle 406 and allows insertion of the catheter 14 into the first elongated clamping receptacle 406 in a snap-fit engagement. The first forward arm 420 and the second forward arm 430 can each be flexible enough to enable slight deformation of the first forward arm 420 and the second forward arm 430 as the first forward arm 420 and the second forward arm 430 are "snapped" onto the catheter 14, but should still be rigid enough to prevent unintentional decoupling of the catheter 14 from the first elongated clamping receptacle 406.

Similarly, the second elongated clamping portion 454 can include a first rear arm 460 having a first rear terminal portion 462 and a second rear arm 470 having a second rear terminal portion 472 that collectively define the second elongated clamping receptacle 456 therebetween. A direction of elongation collectively defined by the first rear arm 460 and the second rear arm 470 of the second elongated clamping portion 454 is denoted by a second vertical line $D3_2$, where the second vertical line $D3_2$ is perpendicular to the receptacle axis D1 and the upper line D2 and is parallel with the first vertical line $D3_1$. The first rear arm 460 and the second rear arm 470 collectively apply the clamping force around shunt valve terminal 22 of the shunt valve 12; in particular, the first rear arm 460 applies a third component $CLAMP_3$ (FIG. 9C) of the clamping force and the second rear arm 470 applies a fourth component $CLAMP_4$ (FIG. 9C) of the clamping force to the shunt valve terminal 22 when the shunt valve terminal 22 is captured at the second elongated clamping receptacle 456, where the third component $CLAMP_3$ and the fourth component $CLAMP_4$ collectively define the consistent circumferential force applied around the shunt valve terminal 22. Similarly, the second elongated clamping portion 454 defines a second opening 455 between the first rear terminal portion 462 of the first rear arm 460 and the second rear terminal portion 472 of the second rear arm 470 that communicates with the second elongated clamping receptacle 456 and allows insertion of the shunt valve terminal 22 into the second elongated clamping receptacle 456. Note that the second opening 455 and the second elongated clamping receptacle 456 of the second elongated clamping portion 454 are wider than the first opening 405 and the first elongated clamping receptacle 406 of the first elongated clamping portion 404 to accommodate the shunt valve terminal 22. Similarly, the first rear arm 460 and the second rear arm 470 can each be flexible enough to enable slight deformation of the first rear arm 460 and the second rear arm 470 as the first rear arm 460 and the second rear arm 470 are "snapped" onto the shunt valve terminal 22, but should still be rigid enough to prevent unintentional decoupling of the shunt valve terminal 22 from the second elongated clamping receptacle 456.

The tensioning portion 408 generates the first component $CLAMP_1$, the second component $CLAMP_2$, the third component $CLAMP_3$ and the fourth component $CLAMP_4$ of the clamping force applied along the catheter 14 and the shunt valve terminal 22. As shown, the tensioning portion 408 defines an exterior surface 482 that can be "smooth" across where the first elongated clamping portion 404 and the second elongated clamping portion 454 meet. Further, the tensioning portion 408 can include an inner curve 484 (FIG. 10D) where the first elongated clamping receptacle 406 meets the second elongated clamping receptacle 456 as shown.

Figure 9A:
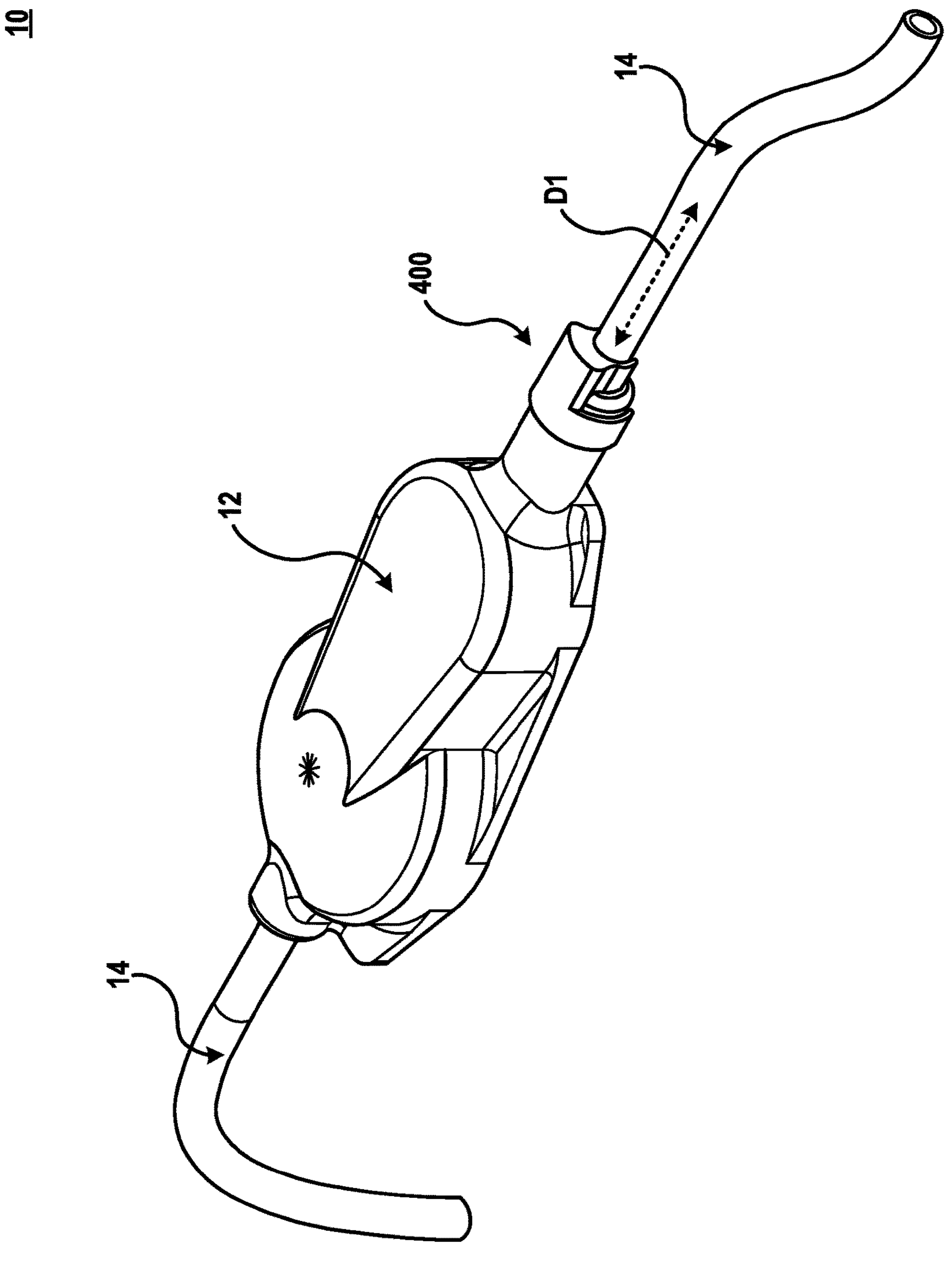
FIG. 9A is an illustration showing a perspective view of a shunt valve system including a third embodiment of a catheter clip.
Figure 9B:
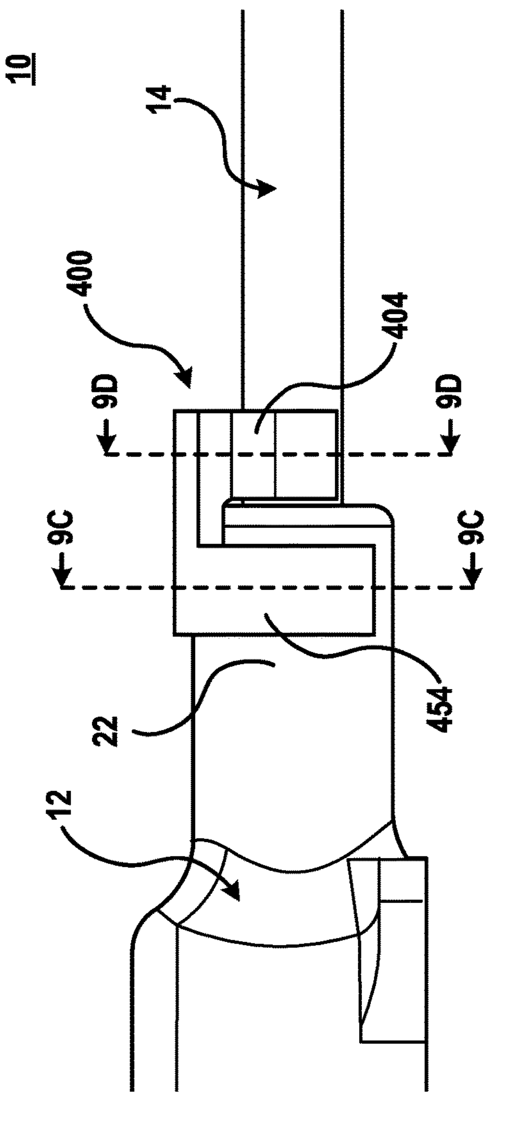
FIG. 9B is an illustration showing a side view of the catheter clip of FIG. 9A coupled around a catheter and a shunt valve of the shunt valve system.
Figure 9D:
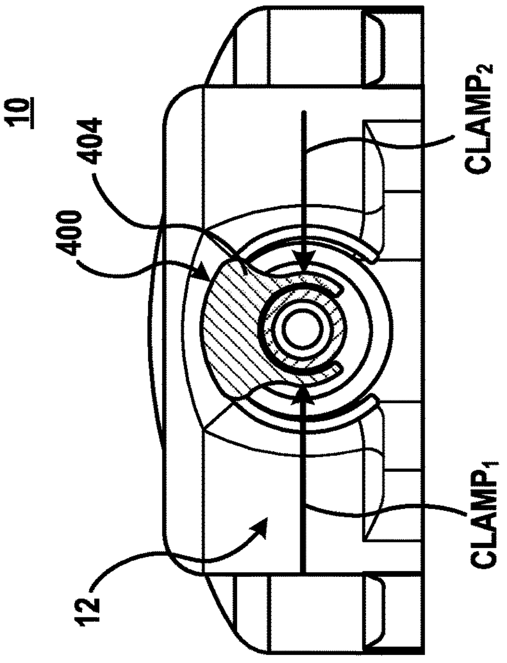
FIGS. 9C and 9D are a pair of cross-sectional front views showing the catheter clip and the shunt valve system of FIG. 9A respectively taken along line 9C-9C and 9D-9D of FIG. 9B.
Figure 9C:
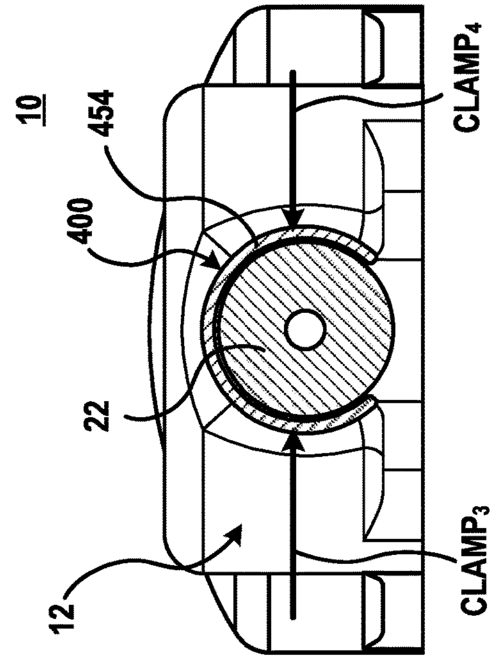
Figure 9E:
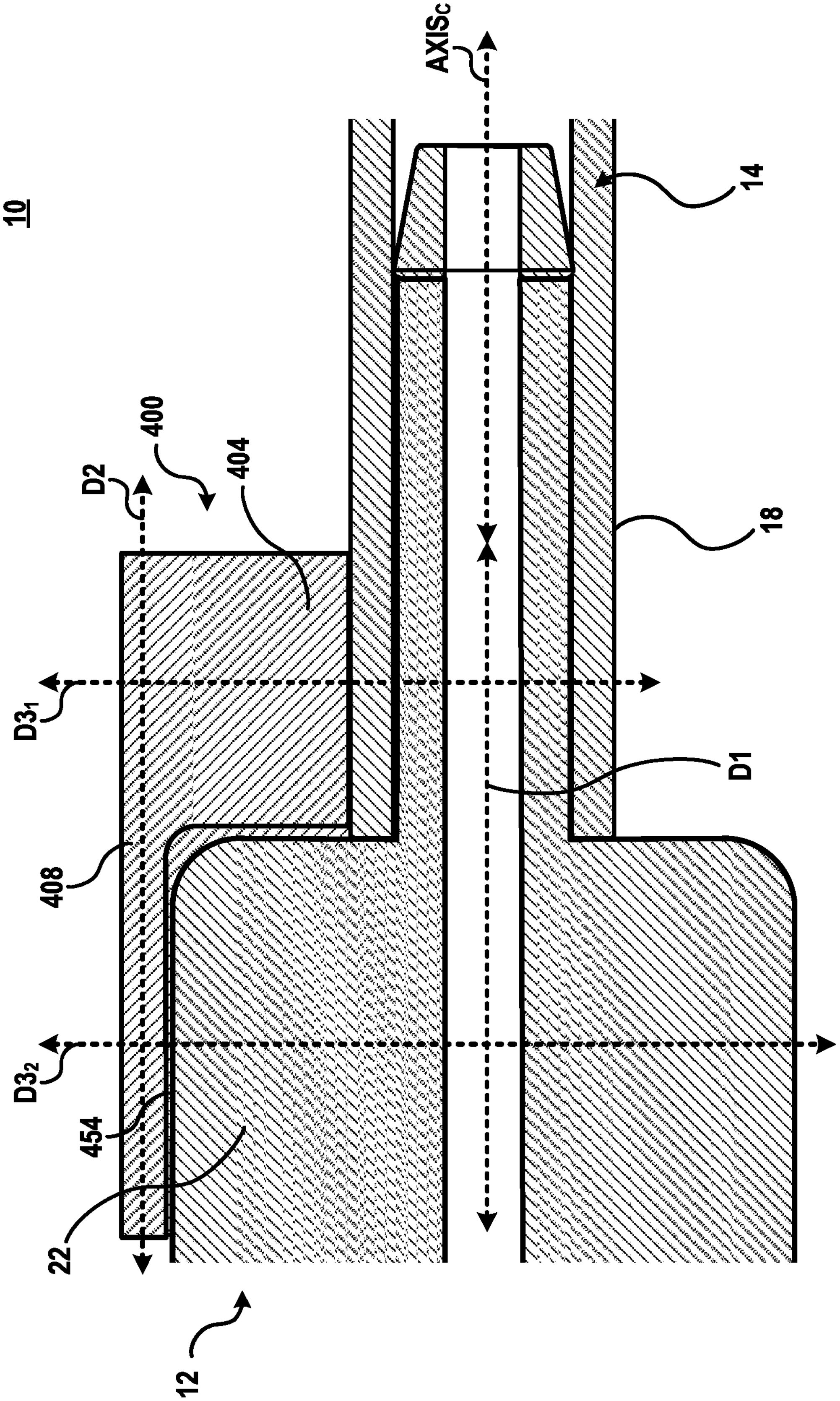
FIG. 9E is an illustration showing a cross-sectional side view showing the catheter clip and the shunt valve system of FIG. 9A.
Figure 9G:
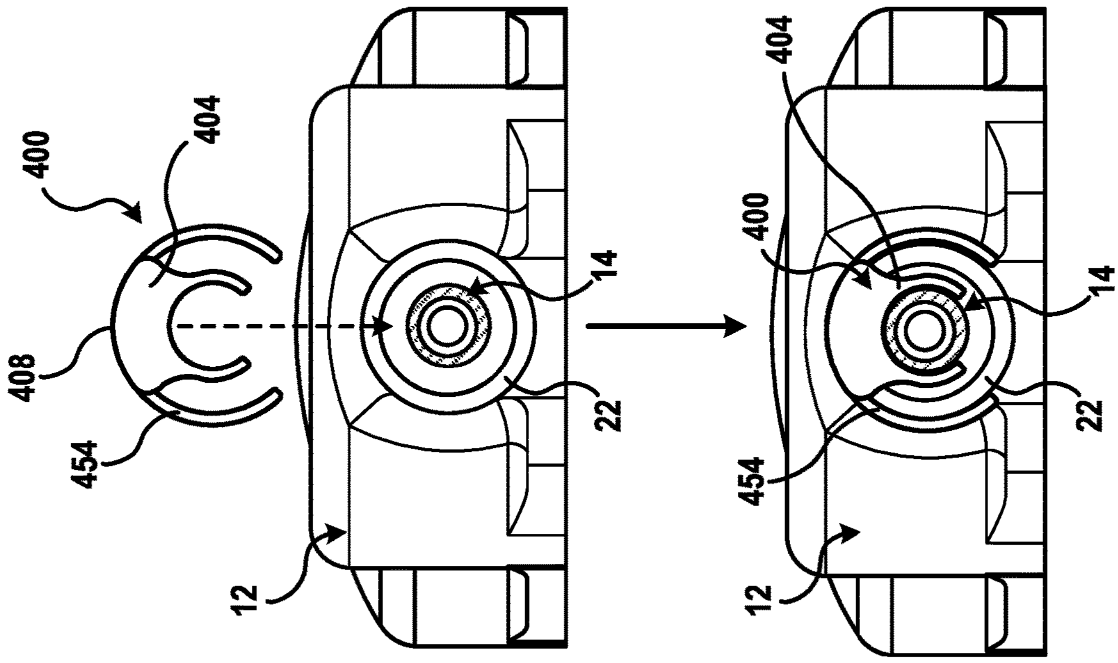
FIGS. 9F and 9G are a pair of side and front views showing a snap-fit engagement of the catheter clip with the shunt valve system of FIG. 9A.
Figure 9F:
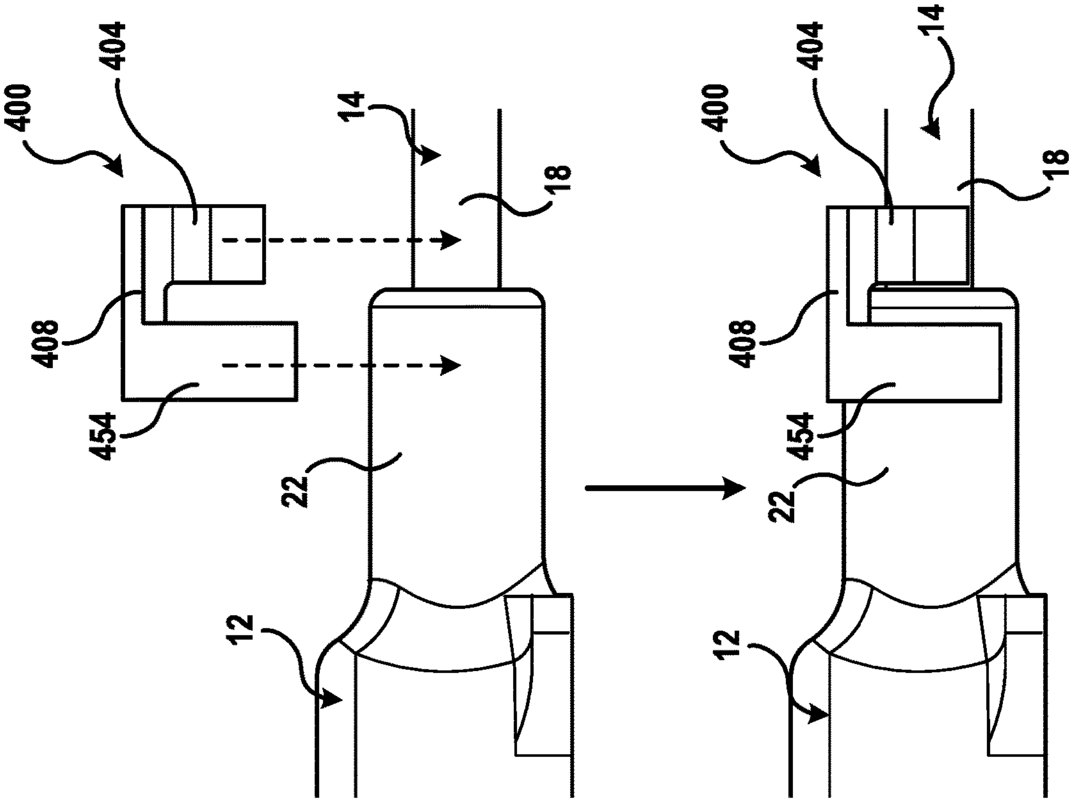
Figure 10B:
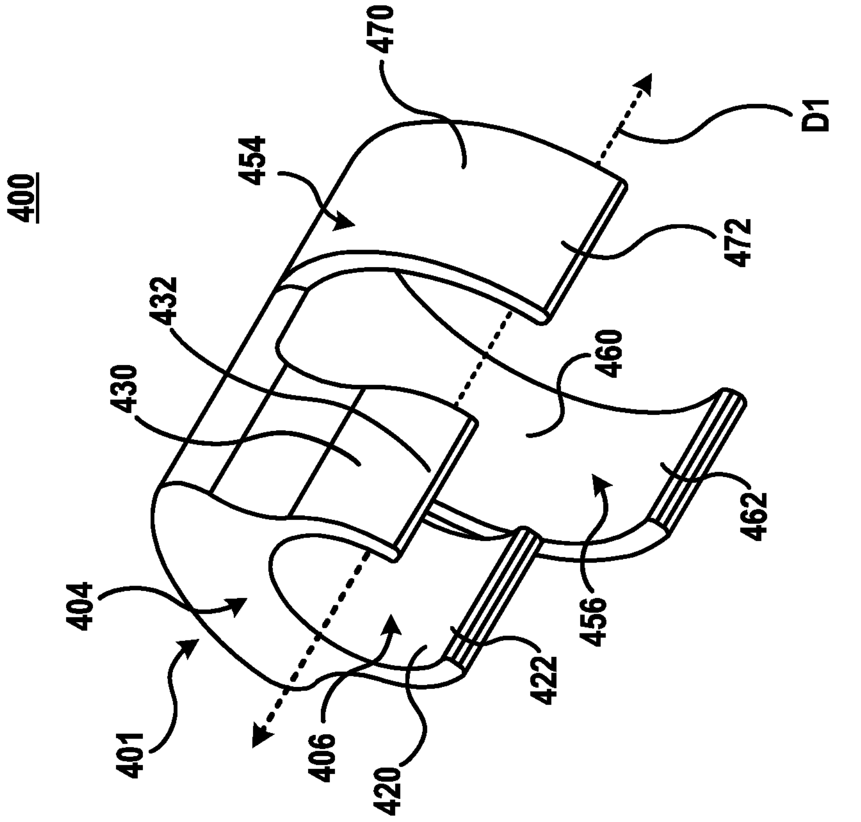
FIGS. 10A and 10B are a pair of top perspective and below perspective views showing the catheter clip of FIG. 9A.
Figure 10A:
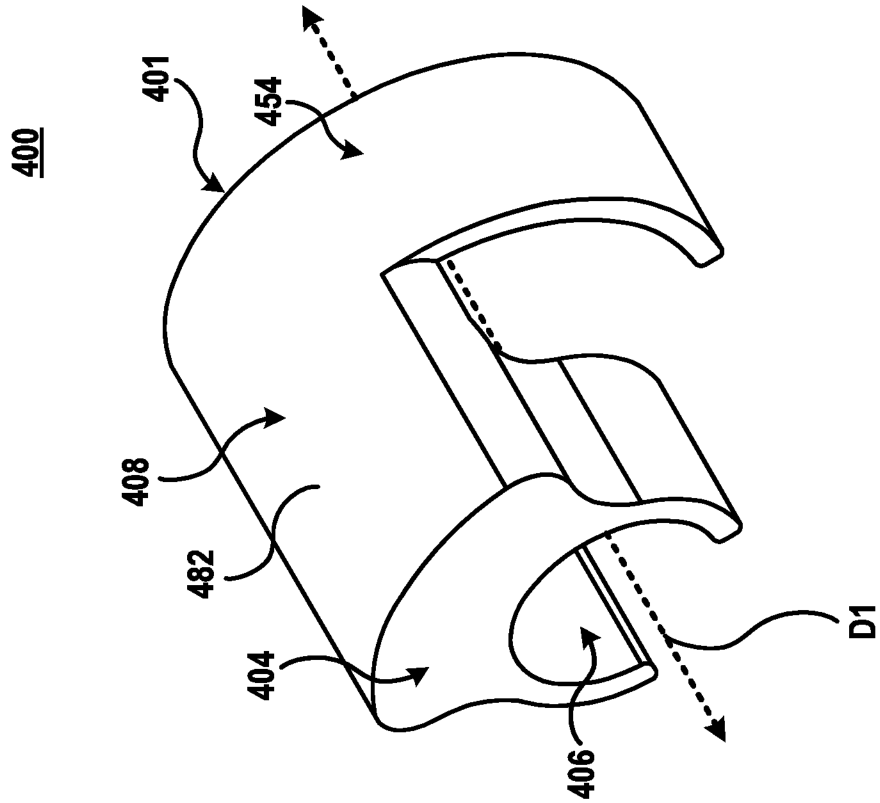
Figure 10D:
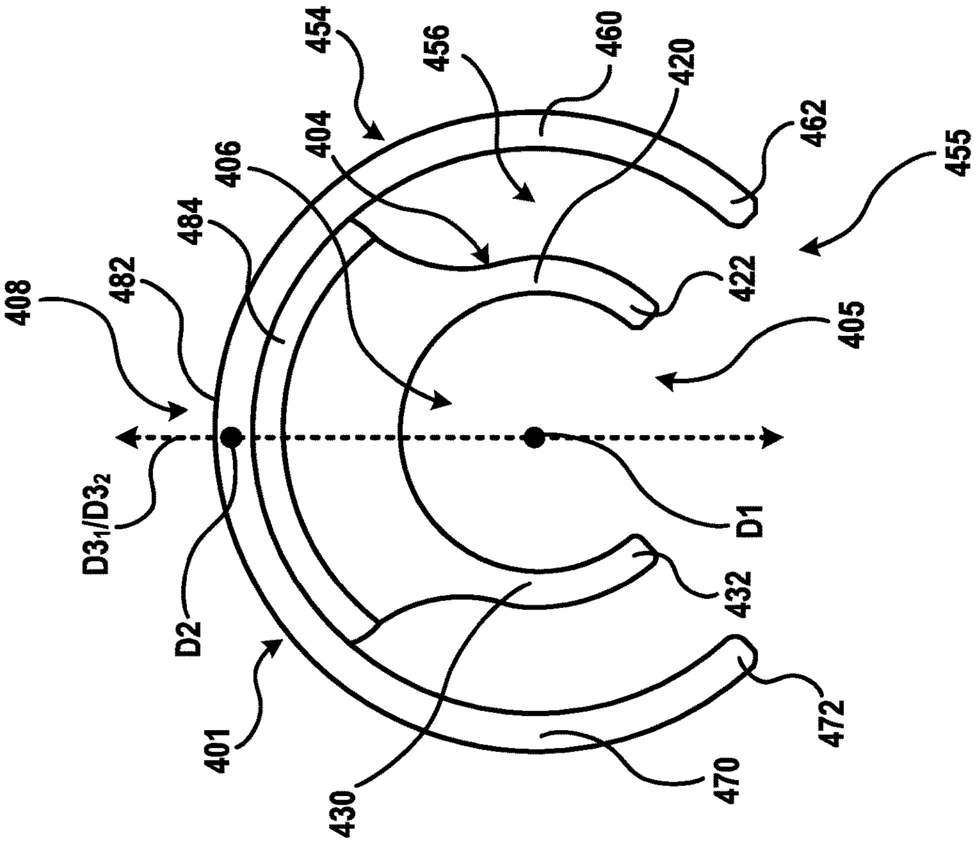
FIGS. 10C and 10D are a pair of front and rear views showing the catheter clip of FIG. 10A.
Figure 10C:
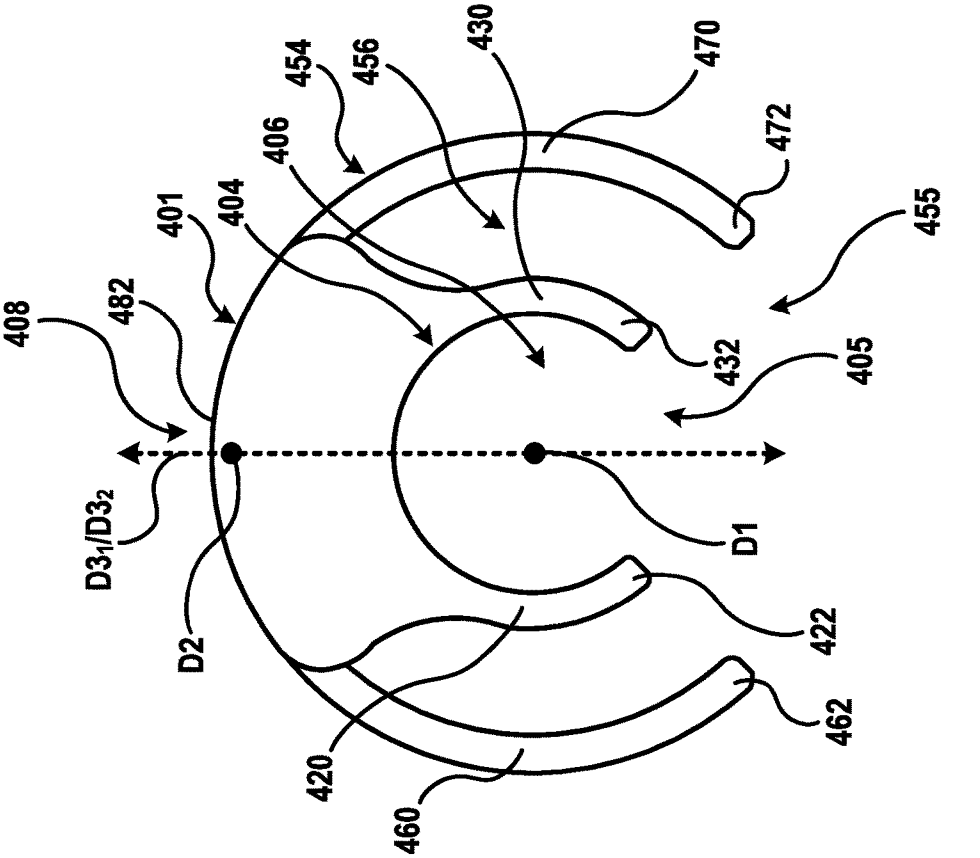
Figure 10E:
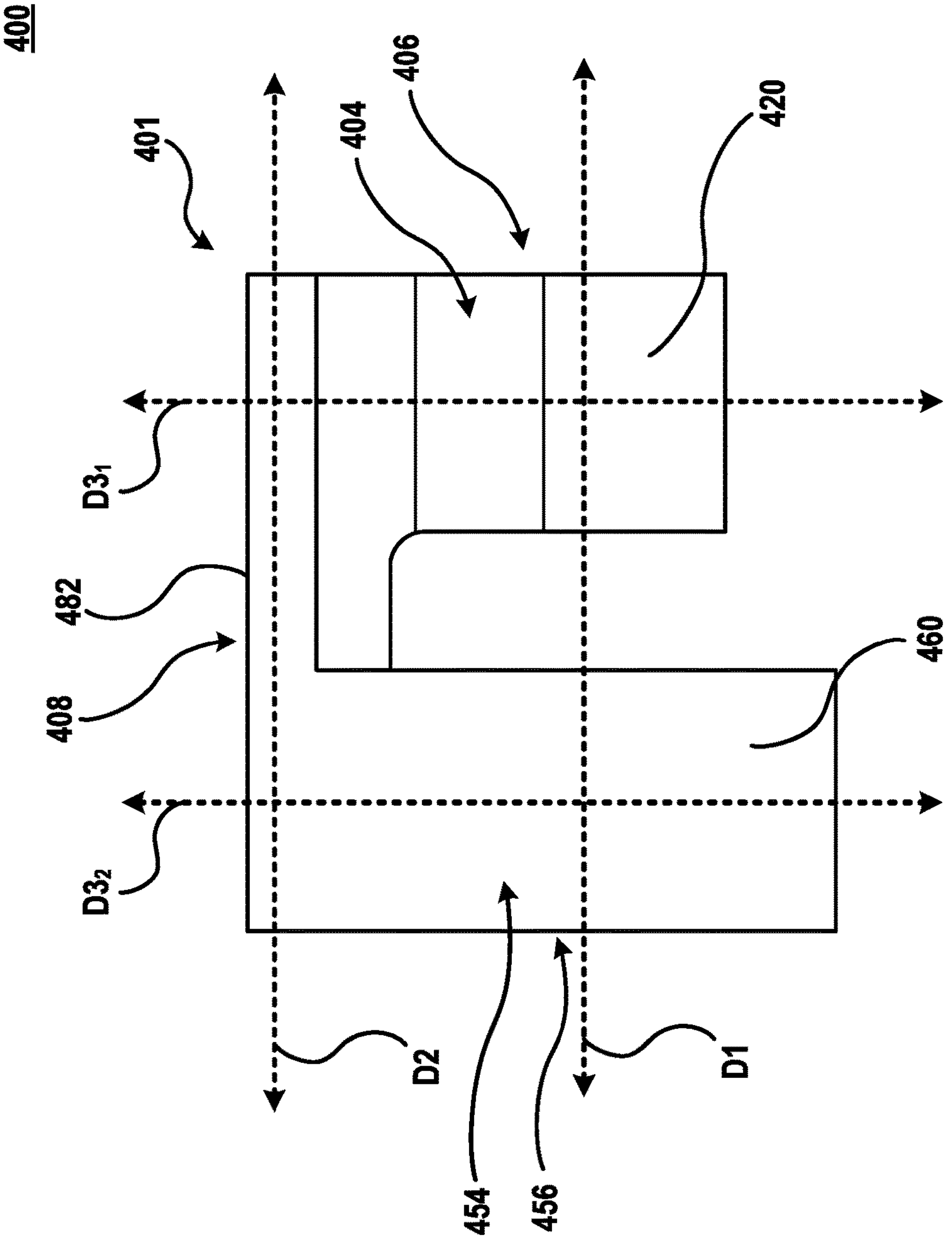
FIG. 10E is a side view showing the catheter clip of FIG. 10A.

In one method of coupling the catheter clip 400 along the shunt valve system 10 as shown in FIGS. 9F and 9G, the catheter clip 400 can "snap" onto the shunt valve terminal 22 and the overlap portion 18 (of the catheter 14) of the shunt valve system 10 by concurrent insertion of the overlap portion 18 into the first opening 405 of the first elongated clamping receptacle 406 and the shunt valve terminal 22 into the second opening 455 of the second elongated clamping receptacle 456. As discussed above, the first forward arm 420, the second forward arm 430, the first rear arm 460, and the second rear arm 470 are each flexible enough to enable slight deformation when "snapping" onto the catheter 14 and the shunt valve terminal 22 while still being rigid enough to prevent unintentional decoupling of the catheter 14 and the shunt valve terminal 22 from the catheter clip 400.

The catheter clip 100, 200, 300 and/or 400 can be made from non-ferrous metals such as titanium, and/or can include high strength plastics such as PEI (polyetherimide).

Figure 11:
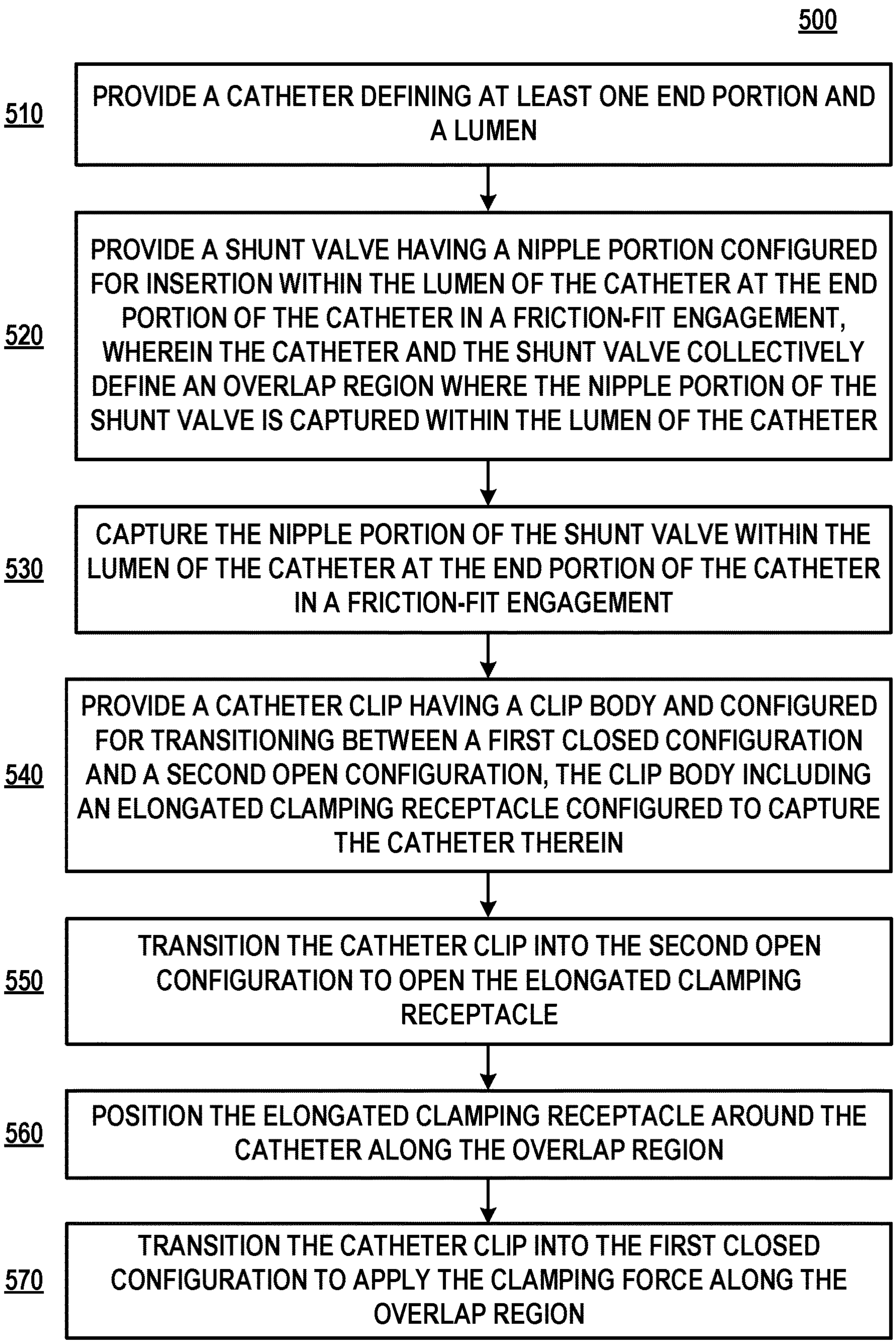
FIG. 11 is a process flow diagram showing a method of securing a catheter of a shunt valve system using the catheter clip of FIGS. 1A, 5A, 7A and 9A.

FIG. 11 shows a method 500 of securing a catheter to a shunt valve of a shunt valve system using the catheter clip 100, 200, 300, and/or 400. Block 510 includes providing a catheter defining at least one end portion and a lumen. Block 520 includes providing a shunt valve having a nipple portion configured for insertion within the lumen of the catheter at the end portion of the catheter in a friction-fit engagement; the catheter and the shunt valve collectively define an overlap region where the nipple portion of the shunt valve is captured within the lumen of the catheter. Block 530 includes capturing the nipple portion of the shunt valve within the lumen of the catheter at the end portion of the catheter in a friction-fit engagement. Block 540 includes providing a catheter clip having a clip body the clip body including an elongated clamping receptacle configured to capture the catheter therein.

Block 550 includes transitioning the catheter clip into the second open configuration to open the elongated clamping receptacle. For the catheter clip 100 of FIGS. 1A-4D, this step can include pinching the first arm and the second arm along the elongated section of the clip body to force the first arm and the second arm apart at the elongated clamping portion. For the catheter clip 200 of FIGS. 5A-6B, this step can include forcing the first arm and the second arm apart at the first terminal portion and the second terminal portion. Similarly, the catheter clip 300 of FIGS. 7A-8F, this step can include forcing the first terminal portion and the second terminal portion apart when the first terminal portion and the second terminal portion are not coupled at the tensioning portion. Note that for the catheter clip 400 of FIGS. 9A-10E, this step can be applied after block 560 discussed below.

Block 560 includes positioning the elongated clamping receptacle around the catheter along the overlap region. For the catheter clip 400 of FIGS. 9A-10E, this step includes positioning the first elongated clamping receptacle around the catheter along the overlap region and simultaneously positioning the second elongated clamping receptacle around the shunt valve along the shunt valve terminal. The "opening" step of block 550 discussed above as applied to the catheter clip 400 is performed after block 560 by "snapping" the catheter clip 400 along the shunt valve system; the first forward arm, the second forward arm, the first rear arm and the second rear arm can all be flexible enough for slight deformation to enable the catheter clip 400 to capture the catheter and the shunt valve terminal within the first elongated clamping receptacle and the second elongated clamping receptacle.

Subsequently, block 570 includes transitioning the catheter clip into the first closed configuration to apply the clamping force along the overlap region. For the catheter clip 100 of FIGS. 1A-4D, this step can include releasing the first arm and the second arm along the elongated section of the clip body to draw the first arm and the second arm together at the elongated clamping portion. For the catheter clip 200 of FIGS. 5A-6B, this step can include drawing the first arm and the second arm together at the first terminal portion and the second terminal portion until the catheter is captured at the elongated clamping portion. For the catheter clip 300 of FIGS. 7A-8F, this step can include drawing the first terminal portion and the second terminal portion together and coupling the first terminal portion and the second terminal portion together at the tensioning portion to form the junction of the first terminal portion and the second terminal portion in a securing arrangement. In particular, to couple the first terminal portion and the second terminal portion together, a practitioner can insert the ratchet protrusion of the first terminal portion into the ratchet receptacle of the second terminal portion such that the ratchet tooth of the plurality of ratchet teeth of the ratchet protrusion engages the tongue protrusion of the ratchet receptacle and can subsequently draw the ratchet protrusion of the first terminal portion through the ratchet receptacle of the second terminal portion until the clamping force applied along the overlap region is sufficient. Similarly, the "closing" step of block 570 as applied to the catheter clip 400 of FIGS. 9A-10E is performed when "snapping" the catheter clip 400 along the shunt valve system after the catheter and the shunt valve terminal are captured within the first elongated clamping receptacle and the second elongated clamping receptacle are captured; the first forward arm, the second forward arm, the first rear arm and the second rear arm are rigid enough to return to their un-deformed configurations and prevent unintentional decoupling of the catheter and the shunt valve terminal from the catheter clip 400.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A catheter clip, comprising:

a clip body including:

an elongated clamping portion at a distal portion of the clip body and having; an elongated clamping receptacle defining a circular cross-section and a receptacle axis and configured to receive a catheter within the elongated clamping receptacle;

a tensioning portion at a proximal portion of the clip body and configured to generate a clamping force at the elongated clamping portion;

a crossed portion having a first lateral portion and a second lateral portion that collectively overlap with the elongated clamping receptacle, the first lateral portion and the second lateral portion being substantially perpendicular with the receptacle axis when in a first "closed" configuration; and the elongated clamping receptacle including a first elongated tab portion extending from the first lateral portion and a second elongated tab portion extending from the second lateral portion, (a) wherein the first elongated tab portion and the second elongated tab portion have opposing directions of elongation that extend substantially parallel to the receptacle axis, (b) wherein respective distal-most surfaces of the first elongated tab portion and the second elongated tab portion are substantially co-planar with a distal-most surface of the first lateral portion, and (c) wherein respective proximal-most surfaces of the first elongated tab portion and the second elongated tab portion are substantially co-planar with a proximal-most surface of the second lateral portion.

2. The catheter clip of claim 1, wherein the clamping force applied at the elongated clamping receptacle is a consistent circumferential force.

3. The catheter clip of claim 1, further comprising:

a first arm and a second arm extending from the tensioning portion that collectively define a central body axis, wherein the central body axis is parallel with the receptacle axis;

wherein the first arm includes a first terminal portion defined opposite to the tensioning portion that connects the first lateral portion with the first elongated tab portion, and the second arm includes a second terminal portion defined opposite to the tensioning portion that connects the second lateral portion with the second elongated tab portion.

4. The catheter clip of claim 3, wherein the tensioning portion of the clip body forms a torsion spring arrangement defining a loop between the first arm and the second arm that generates a biasing force associated with the clamping force, wherein the biasing force applied by the tensioning portion to the first arm and the second arm forces the first arm and the second arm apart from one another.

5. The catheter clip of claim 4, wherein the first arm and the second arm collectively define an elongated section extending from the tensioning portion and the crossed portion associated with the elongated clamping portion that inverts the biasing force generated by the tensioning portion into the clamping force that draws the first arm and the second arm together at the elongated clamping portion to apply the clamping force around the catheter when the catheter is captured at the elongated clamping portion.

6. The catheter clip of claim 5, wherein the elongated clamping portion can transition from the first "closed" configuration to a second "open" configuration when the first arm and the second arm are pinched together along the elongated section and wherein the elongated clamping portion can transition from the second "open" configuration to the first "closed" configuration when the first arm and the second arm are released.

7. The catheter clip of claim 5, wherein the first arm defines a first terminal bend between the crossed portion of the clip body and the first terminal portion of the first arm, the first terminal bend defining a perpendicular angle relative to the receptacle axis and the central body axis; and wherein the second arm defines a second terminal bend between the crossed portion of the clip body and the second terminal portion of the second arm, the second terminal bend defining a perpendicular angle relative to the receptacle axis and the central body axis.

8. The catheter clip of claim 3, wherein the elongated clamping portion defines a first clamping element at the first terminal portion of the first arm and a second clamping element at the second terminal portion of the second arm.

9. The catheter clip of claim 3, wherein the first arm includes a first slot and the second arm includes a second slot that collectively enable a practitioner to grip the first arm and the second arm to transition the elongated clamping portion from the first "closed" configuration to a second "open" configuration such that the first arm and the second arm are forced apart, and to transition the elongated clamping portion from the second "open" configuration to the first "closed" configuration such that the first arm and the second arm are drawn towards one another.

10. The catheter clip of claim 1, the first lateral portion and the second lateral portion being substantially parallel with one another and having opposing directions of elongation when in a closed configuration.

11. The catheter clip of claim 1, the first lateral portion and the second lateral portion being substantially coplanar with one another when in a closed configuration.

12. The catheter clip of claim 1, the crossed portion collectively defining an upper portion of the elongated clamping receptacle, and the first elongated tab portion and the second elongated tab portion collectively defining a lower portion of the elongated clamping receptacle.

13. The catheter clip of claim 12, wherein the first lateral portion of the crossed portion defines a distal section of the upper portion of the elongated clamping receptacle; and wherein the second lateral portion of the crossed portion defines a proximal section of the upper portion of the elongated clamping receptacle.

14. A system, comprising:

a catheter defining an end portion and a lumen;

a shunt valve having a nipple portion configured for insertion within the lumen of the catheter at the end portion of the catheter in a friction-fit engagement, wherein the catheter and the shunt valve define an overlap region where the nipple portion of the shunt valve is captured within the lumen of the catheter; and a catheter clip having a clip body and configured for transitioning between a first closed configuration and a second open configuration, the clip body including:

an elongated clamping portion having an elongated clamping receptacle, the elongated clamping receptacle defining a circular cross-section and a receptacle axis and configured to receive the catheter within the elongated clamping receptacle at the overlap region;

a tensioning portion configured to generate a clamping force at the elongated clamping portion when the clip body is in the first closed configuration, wherein the clamping force applied at the elongated clamping receptacle is a consistent circumferential force; and a crossed portion having a first lateral portion and a second lateral portion that collectively overlap with the elongated clamping receptacle, the first lateral portion and the second lateral portion being substantially perpendicular with the receptacle axis when in a closed configuration;

the elongated clamping receptacle including a first elongated tab portion extending from the first lateral portion and a second elongated tab portion extending from the second lateral portion, (a) wherein the first elongated tab portion and the second elongated tab portion have opposing directions of elongation that extend substantially parallel to the receptacle axis, (b) wherein respective distal-most surfaces of the first elongated tab portion and the second elongated tab portion are substantially co-planar with a distal-most surface of the first lateral portion, and (c) wherein respective proximal-most surfaces of the first elongated tab portion and the second elongated tab portion are substantially co-planar with a proximal-most surface of the second lateral portion.

15. The system of claim 14, further comprising:

a first arm defining a first terminal portion that connects the first lateral portion with the first elongated tab portion of the clip body and a second arm defining a second terminal portion that connects the second lateral portion with the second elongated tab portion of the clip body, wherein the first arm and the second arm are connected at the tensioning portion.

16. The system of claim 15, wherein the first arm and the second arm collectively define a central body axis that is parallel with the receptacle axis.

17. A method, comprising:

providing a catheter defining an end portion and a lumen;

providing a shunt valve having a nipple portion configured for insertion within the lumen of the catheter at the end portion of the catheter in a friction-fit engagement, wherein the catheter and the shunt valve collectively define an overlap region where the nipple portion of the shunt valve is captured within the lumen of the catheter;

providing a catheter clip having a clip body and configured for transitioning between a first closed configuration and a second open configuration, the clip body including:

an elongated clamping receptacle having a receptacle axis and configured to capture the catheter therein;

a crossed portion having a first lateral portion and a second lateral portion that collectively define an upper portion of the elongated clamping receptacle, the first lateral portion and the second lateral portion being substantially perpendicular with the receptacle axis when in the first closed configuration; and a first elongated tab portion extending from the first lateral portion and a second elongated tab portion extending from the second lateral portion that collectively define a lower portion of the elongated clamping receptacle, (a) wherein the first elongated tab portion and the second elongated tab portion have opposing directions of elongation that extend substantially parallel to the receptacle axis, (b) wherein respective distal-most surfaces of the first elongated tab portion and the second elongated tab portion are substantially co-planar with a distal-most surface of the first lateral portion, and (c) wherein respective proximal-most surfaces of the first elongated tab portion and the second elongated tab portion are substantially co-planar with a proximal-most surface of the second lateral portion;

transitioning the catheter clip into the second open configuration to open the elongated clamping receptacle;

positioning the elongated clamping receptacle around the catheter along the overlap region; and transitioning the catheter clip into the first closed configuration to apply a clamping force along the overlap region.

18. The method of claim 17, further comprising:

capturing the nipple portion of the shunt valve within the lumen of the catheter at an end portion of the catheter in a friction-fit engagement.

* * * * *